(12) United States Patent
Gerashchenko et al.

(10) Patent No.: US 10,226,425 B2
(45) Date of Patent: Mar. 12, 2019

(54) PHARMACEUTICAL PREPARATION AND METHOD OF ITS PRODUCTION AND USE

(71) Applicants: Igor Gerashchenko, Rorschach (CH); Oleksii Chepliaka, Rorschach (CH); invenres GmbH, Rorschach (CH)

(72) Inventors: Igor Gerashchenko, Rorschach (CH); Oleksii Chepliaka, Rorschach (CH)

(73) Assignee: invenres GmbH, Rorschach (CH)

( * ) Notice: Subject to any disclaimer, the term of this patent is extended or adjusted under 35 U.S.C. 154(b) by 0 days.

(21) Appl. No.: 15/034,615

(22) PCT Filed: Nov. 4, 2014

(86) PCT No.: PCT/EP2014/073698
§ 371 (c)(1),
(2) Date: May 5, 2016

(87) PCT Pub. No.: WO2015/067603
PCT Pub. Date: May 14, 2015

(65) Prior Publication Data
US 2016/0271294 A1 Sep. 22, 2016

(30) Foreign Application Priority Data
Nov. 6, 2013 (EP) ..................... 13191810

(51) Int. Cl.
| | |
|---|---|
| A61L 26/00 | (2006.01) |
| A61L 15/22 | (2006.01) |
| A61L 15/60 | (2006.01) |
| A61L 15/32 | (2006.01) |
| A61L 15/26 | (2006.01) |
| A61L 15/44 | (2006.01) |
| A61L 15/18 | (2006.01) |
| A61L 15/28 | (2006.01) |
| A61K 9/14 | (2006.01) |
| A61K 9/00 | (2006.01) |
| A61K 9/16 | (2006.01) |
| A61K 31/167 | (2006.01) |
| A61K 31/5415 | (2006.01) |
| A61K 38/48 | (2006.01) |
| A61K 45/06 | (2006.01) |

(Continued)

(52) U.S. Cl.
CPC ............ *A61K 9/143* (2013.01); *A61K 9/0014* (2013.01); *A61K 9/145* (2013.01); *A61K 9/146* (2013.01); *A61K 9/1611* (2013.01); *A61K 9/1641* (2013.01); *A61K 31/167* (2013.01); *A61K 31/5415* (2013.01); *A61K 38/48* (2013.01); *A61K 45/06* (2013.01); *A61L 15/18* (2013.01); *A61L 15/225* (2013.01); *A61L 15/26* (2013.01); *A61L 15/28* (2013.01); *A61L 15/32* (2013.01); *A61L 15/44* (2013.01); *A61L 15/60* (2013.01); *A61L 26/0004* (2013.01); *A61L 26/008* (2013.01); *A61L 26/0019* (2013.01); *A61L 26/0023* (2013.01); *A61L 26/0038* (2013.01); *A61L 26/0052* (2013.01); *A61L 26/0066* (2013.01); *C08G 77/04* (2013.01); *C08G 77/06* (2013.01); *A61L 2300/402* (2013.01); *A61L 2300/404* (2013.01); *A61L 2300/406* (2013.01); *A61L 2300/412* (2013.01); *A61L 2300/45* (2013.01); *A61L 2300/606* (2013.01); *A61L 2300/62* (2013.01); *A61L 2400/04* (2013.01); *A61L 2420/06* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 8,466,228 B2 * | 6/2013 | Smith | ................. | A61L 15/60 |
| | | | | 524/430 |
| 2004/0092415 A1 * | 5/2004 | Focht | ................. | A61K 8/02 |
| | | | | 510/130 |
| 2010/0240532 A1 | 9/2010 | Tolcheyev et al. | | |

(Continued)

FOREIGN PATENT DOCUMENTS

| | | |
|---|---|---|
| CN | 101772356 A | 7/2010 |
| CN | 102811724 A | 12/2012 |

(Continued)

OTHER PUBLICATIONS

Huang et al., "Risk of Methicillin-Resistant *Staphylococcus aureus* Infection after Previous Infection or Colonization", clinical Infectious Diseases, vol. 2003, No. 36, pp. 281-285 (Jan. 2003).
Kaye et al., "The Deadly Toll of Invasive Methicillin-Resistant *Staphyloccus aureus* Infection in Community Hospitals", Clinical Infectious Diseases, vol. 46, pp. 1568-1577 (Apr. 3, 2008).
Furr. et al., "Antibacterial Activity of Actisorb Plus, Actisorb and Silver Nitrate", Journ. of Hospital In Infection, vol. 27, No. 3, pp. 201-208 (1994).

(Continued)

*Primary Examiner* — Robert A Wax
*Assistant Examiner* — Danah Al-Awadi
(74) *Attorney, Agent, or Firm* — Panitch Schwarze Belisario & Nadel LLP

(57) ABSTRACT

Thus, the present invention provides a composition in powder form comprising highly dispersed silica particles, polymethylsiloxane particles, and at one or both of a cationic surfactant and an antimicrobial substance, wherein at least 25% by weight of the cationic surfactant is present in primary polymethylsiloxane particles carrying the cationic surfactant on their surface and/or in agglomerates of these primary particles, and/or at least 25% by weight, of the antimicrobial substance is present in primary highly dispersed silica particles carrying the antimicrobial substance on their surface and/or in agglomerates of these primary particles.

17 Claims, 3 Drawing Sheets

(51) Int. Cl.
  C08G 77/04    (2006.01)
  C08G 77/06    (2006.01)

(56) References Cited

U.S. PATENT DOCUMENTS

2010/0291062 A1    11/2010  Golub et al.
2013/0058880 A1*    3/2013  Dong .................. C08K 5/5419
                                                        424/63
2016/0206709 A1*    7/2016  Golub .................. A61K 9/1676

FOREIGN PATENT DOCUMENTS

| EP | 1721662 A1 | | 11/2006 |
|---|---|---|---|
| EP | 2277559 | * | 1/2011 |
| EP | 2476420 | * | 7/2012 |
| UA | 32088 | * | 12/2000 |
| UA | 32088 C2 | | 12/2000 |
| UA | 32774 | * | 12/2000 |
| UA | 82774 C2 | | 5/2008 |
| WO | WO 2008051513 | * | 5/2008 |
| WO | 2010079209 A2 | | 7/2010 |

OTHER PUBLICATIONS

Bradley et al., "Systematic Reviews of Wound Care Management: (2) Dressings and Topical Agents Used in the Healing of Chronic Wounds", HTA Programme, vol. 3, No. 17, Pt. 2, 143 pages (1999).
Baksa, "Selection of Wound Dressings", J. Orvosi Hetilap, vol. 141, No. 47, pp. 2549-2554 (2000).
Blitz, "Surface Chemistry in Biomedical and Enviromental Science", NATO Science Series, vol. 228 458 pages (2006).
Fleck, "Palliative Dilemmas: Wound Odour", Wound Care Canada, vol. 4, No. 3, pp. 10-13 (2006).
Woo et al., "Local Wound Care for Malignant and Palliative Wounds", Advances in Skin & Wound Care: Journ. for Prevention and Healing, vol. 23, No. 9, pp. 417-428 (Sep. 2010).
Lemaire et al., "Activity of Fusidic Acid Against Extracellular and Inracellular *Staphylococcus aureus*: Influence of pH and Comparison with Linezolid and Clindamycin", Clinical Infectious Diseases, vol. 52, Suppl. 7, pp. S493-S503 (2011).
Sutherland et al., "Antibacterial Activity of Mupirocin (Pseudomonic Acid), a New Antibiotic for Topical Use", Antimicrobial Agents and Chemo., vol. 27, No. 4, pp. 495-498 (Apr. 1985).
Council of Europe, "Bacitracin" European Pharmacopoeia, vol. 5., Suppl. 5.1 and 5.2, pp. 1245-1247, (2005).
Int'l Search Report and Written Opinion dated Jan. 16, 2015 in Int'l Application No. PCT/EP2014/073698.
Chuiko et al., "Application Efficiency of Complex Preparations Based on Nanodisperse Silica in Medical Practice", Springer Science, pp. 53-62, (Jan. 1, 2009).
Goryunov et al., "Purulent Surgery: Atlas", Binom. Laboratory of Science, pp. 504-506 (2004).
Donaldson et al, "Ciprofloxacin in General Practice," BMJ (Clinical Research Ed.), vol. 308, pp. 1437 (May 1994).
"Silica, Colloidal Hydrated", European Pharm. 6.0, 1 page, (2008).
Moore, "Silicon Dioxide", Pharmacopeial Forum, vol. 31, No. 4, pp. 1205 (2007).
Chepliaka, "Complex Treatment of Anorectal Abscess Patients," Dissertation of PhD Vinitsa, 3 pgs (2006) (English Summary).
Azuma et al., "Immunological Modulation by Lidocaine-Epinephrine and Prilocaine-Felypressin on the Functions Related to Natural Immunity in Neutrophils and Macrophages", Current Drug Targets, Immun. Endocrine and Metabolic Disorders, vol. 4, No. 1, 1 pg (2004) (Abstract Only).
Skorkowska-Telichowska et al., "The Local Treatment and Available Dressings Designed for Chronic Wounds", J. Am Acad. Dermatol., vol. 68, No. 4, pp. 117-126 (2013).
Rutkovskii et al., "Rationale of the Application of Sorption-Lymphatic Techniques in the Treatment of Anorectal Abscess", Lecture on IV Republican Scientific Practical Conference with Participation of International Proctologists "Functional and Inflectional Diseases of Large Intestine: Surgical and Therapeutic Aspects. New in Coloproctology", pp. 78-79 (2001).
Chuiko et al., "Medical Aspects of Application of Highly Disperse Amorphous Silica," Surface Chemistry in Biomedical and Environmental Science, Ed. Biltz et al., pp. 191-204. (2006).
Office Action dated Jun. 21, 2018 in CN Application No. 201480072167.7.

* cited by examiner

PHARMACEUTICAL PREPARATION AND METHOD OF ITS PRODUCTION AND USE

CROSS REFERENCE TO RELATED APPLICATION

This application is a Section 371 of International Application No. PCT/EP2014/073698, filed Nov. 4, 2014, which was published in the English language on May 14, 2015, under International Publication No. WO 2015/067603 A1 and the disclosure of which is herein incorporated by reference in its entirety.

TECHNICAL FIELD

The invention relates to new compositions based on synthetic highly dispersed silicas and polymethylsiloxane that have high sorptive, anti-inflammatory and wound-healing abilities that can be used in different fields of practical medicine for the treatment of diseases which are caused by pathogenic microorganisms, in particular, purulent wounds.

Clinical practice shows that the treatment of purulo-inflammatory diseases and purulent wounds by using modern antimicrobial agents only does not always lead to the desired result. Misuse of antibiotics contributes to the emergence of resistant (hospital) strains of pathogenic microorganisms, including methicillin-resistant *Staphylococcus aureus* (MRSA), which is a serious challenge for modern medicine in general [Huang S S, Platt R., "Risk of methicillin-resistant *Staphylococcus aureus* infection after previous infection or colonization", Clin. Infect. Dis., 2003, vol. 36, p. 281-285; Kaye K, Anderson D, Choi Y, et al., "The deadly toll of invasive methicillin-resistant *Staphylococcus aureus* infection in community hospitals", Clin. Infect. Dis., 2008, vol. 46, p. 1568-1577].

The intensity of the regeneration process and healing of infected ulcers and wounds depends largely on the speed at which they are cleared from the pus and necrotic tissues. For this purpose applique sorption, i.e., a method of wound healing in which a sorbent in powder form is applied to the wound as a powder dressing, also known as sorption-applique treatment, can be used. Applique sorption is a kind of sorption detoxification which accelerates wound healing and restores the integrity of the skin and mucous membranes by the removal of microbial cells, bacterial toxins and toxic metabolites of wound fluid and wound cavities in direct contact with the surface of the sorptive preparation [Sorbents and Their Clinical Applications (Ed. C. Giordano), New-York-London, Academic Press, 1980]. An important therapeutic factor in the first phase of wound healing is also seen in the dehydration, i.e., absorption of fluid from the wound cavity and perifocal tissues.

BACKGROUND ART

As sorption preparations for topical treatment of wounds materials based on activated carbon, various swelling polymers of synthetic and natural origin and silicon sorbents, such as sorbents derived from silica and silicone compounds, have been proposed.

Among the carbon preparations for wound healing Actisorb Plus (Johnson & Johnson) is particularly well-known, which is an activated carbon fiber coated with colloidal silver. Actisorb Plus has a nonspecific antimicrobial effect due to silver and the carbon sorbent can absorb pathogenic metabolites that accumulate in the wound contents. The preparation is used primarily for the healing of superficial wounds and skin defects, such as venous ulcers [Furr J. R., Russell A. D., Turner T. D., Andrews A., "Antibacterial activity of Actisorb Plus, Actisorb and silver nitrate", J. Hosp. Infect., 1994, vol. 27(3), p. 201-208]. However, activated carbon having nanometer pore size cannot absorb large protein molecules, which include bacterial toxins and tissue degradation products.

Methods of sorption-applique treatment of purulent wounds by complex sorbent SUMS-1 (Activated charcoal+Aluminium oxide) with immobilized metronidazole [Rutkovskiy E. A., Shtofin S. G., Lubarskiy M. S., Yakushenko V. K., "Grounding for application of sorption lymphogenous methods in healing of anorectal abscess", Lecture on IV Republican scientific practical Conference with participation of international proctologists "Functional and inflectional diseases of large intestine: surgical and therapeutic aspects. New in coloproctology" (6-7 Sep. 2001)—Minsk—2001. p. 78-79] or enzymes (nigedase and hyaluronidase) have been proposed. Due to their pronounced porous structure activated carbon sorbents absorb substances of low and medium molecular weight. Metronidazole exhibits a high sensitivity towards anaerobic microflora, which is usually seen in anorectal abscesses. However SUMS-1 has limited sorption capacity, low rates of water absorption and pathogenic proteins absorption due its structure, so that it does not have anti-inflammatory properties. The duration of the nigedase and hyaluronidase action for a surface sorption-applicative detoxification in the first phase of wound healing is small (less than 16 hours), resulting in shortened fibrinolysis and necrolytic effects that reduce the effectiveness of the therapy and increase the duration of treatment [Lubarskiy M. S., Letyagin A. Y., Gabitov V. H., Semko V. V., Povazhenko A. A., "Sorption mineral carbon preparations in purulent-septic surgery", Russian Academy of Medical Sciences. Institute of Clinical and Experimental lymphology—Bishkek, Novosibirsk, St. Petersburg, 1994].

The disadvantage of carbon adsorbents if applied to wounds is that two to three hours after application onto a wound, they start forming a crust that prevents the outflow from the wound, and the adsorption process is greatly reduced. Part of the granules is introduced into the tissue and cannot be removed. The surface of the granules is coated with fragments of cells and protein molecules, which also reduces their adsorptive activity [Alimov M. M., Experience in application carbon sorbent in treatment complicated soft tissue wounds/Alimov M. M., Bahtiyarov O. R., Batyrov D. Sh. Sorption methods of detoxification and immune correction in Surgery: Collection of treatises. —Tashkent, 1984, p. 173-174].

Wound dressings are designed to keep the wound clean and free from contamination and also to promote wound healing, particularly in chronic wounds where there may be significant tissue loss, e.g.: hydrocolloid dressings, hydrogels, alginate dressings and others [Skorkowska-Telichowska K., Czemplik M., Kulma A., Szopa J., "The local treatment and available dressings designed for chronic wounds", J. Amer. Acad. Dermatol., 2013, vol. 68(4), p. 117-126].

There is good evidence to suggest that hydrocolloid dressings are preferential to traditional therapies (i.e. saline gauze and antiseptics) for the treatment of pressure sores, but there may be publication bias, which may have resulted from more trials with positive results being published than those with negative results. Where topical agents have been compared with a placebo for the treatment of pressure sores there is no evidence to suggest that the active treatment has a pronounced effect on healing. Comparisons between topical agents and dressings for the treatment of pressure sores suggest that the application of a topical hydrogel more efficiently promotes the healing than that experienced with an early hydrocolloid dressing but not when compared with the improved formulation of the dressing. Comparisons between dressings were unable to show any statistically significant difference in healing rates. Topical agents were, on the whole, not found to expedite the healing of venous leg ulcers [Bradley M., Cullum N., Nelson E. A. et al., "Systematic reviews of wound care management: (2) Dressings and topical agents used in the healing of chronic wounds", Health Technol. Assess., 1999, vol. 3(No. 17, Pt. 2)].

«Geleving» is a basis of draining sorbents with an active mechanism of sorption and comprises a polyvinyl alcohol crosslinked with glutaraldehyde. The polymer has a structure that creates an irreversible sorption capacity for purulent wounds of 14-16 g/g. To reduce the multi pathogenetic effects on the purulent wound, immobilized preparations comprising bioactive draining sorbents that provide a chemotherapeutic wound cleansing (Diotevin, Anilodiotevin) are promising. They create conditions for prolonged release of the wound medications, such as antibiotics, antiseptics, proteolytic enzymes, local anesthetics. When these are applied to richly exuding wounds and brought into contact with the wound, they discharge biologically active sorbents which swell and become a coarse, easily removable gel. Release of the preparations occurs within one day and about 60% of the administered preparations are absorbed into the wound during the first hour. Antimicrobial agents such as Dioxidine can provide suppression of gram positive, gram negative and anaerobic microflora in the wound. Proteolytic enzymes (collagenase, terrylitine) contribute to the lysis of necrotic tissue. However, if the swollen sorbent granules are not carefully removed from the wounds having complex structure, with deep pockets and cavities, there are complications in applicative sorption therapy. Closure of the wound edges and encapsulation of large amounts of sorbent granules which represent a foreign body can lead to a recurrence of the purulent process or the formation of a fistula [Goryunov S. V., Romashov D. V., Butivshchenko, I. A.; under redaction of PhD Abramov M., "Purulent surgery: Atlas", BINOM. Laboratory of science, 2004, p. 504-506].

Also among sorbents the xerogel of methylsilicic acid—hydrophobic polymethylsiloxane is known that provides local wound detoxification due to active sorption of pathogens and low and middle molecular metabolites. Wound exudate fluid is "drained" through a capillary net of the powdered sorbent and organic substances are absorbed into its granules. By raising the pH of the wound it also potentiates the action of a specific antibiotic. Polymethylsiloxane can be used for the applique sorption with or without antibiotics immobilized on its surface. Exemplary preparations are Imosgent and Gentaxan in which the polymethylsiloxane surface is modified by gentamicin [Znamenskiy V. A., Vozianov A. F., Vozianova Zh. M. et al., Application of therapeutic preventive preparation produced on the silica based sorbents. Methodological recommendations, Kiev, 1994, p. 14]. However, in the case of hydrophobic materials, the exudate is not absorbed and spreads rapidly under the bandage which promotes skin maceration and activation of the inflammatory process in the wound [Baksa J., "Selection of wound dressings", J. Orvisi Hetilap., 2000, vol. 141(47), p. 2549-2554].

Hydrophilic highly dispersed silica (HDS) can be used in the first phase of wound healing. Its detoxifying action is due to the ability to absorb pathogenic protein substances (up to 800 mg/g), including microbial enzymes, endo- and exotoxins and microorganisms. The surface of the silica is covered with hydroxyl groups that can bind water molecules, so it produces a pronounced dehydrating effect on the tissue that is essential for the removal of edema as part of the inflammatory process. However, silica, due to lack of porous structure, does not absorb low and middle molecular weight toxic metabolites. HDS does not show direct antimicrobial action, however, it was found that the sensitivity of pathogenic organisms to antibiotics is increased in the presence of HDS [Blitz J. P. and Gun'ko V. M. (eds.), Surface Chemistry in Biomedical and Environmental Science, Springer, 2006, p. 191-204].

Noteworthy is a combination of hydrophilic and hydrophobic sorbents, providing sorption of a wide range of substances and pathogenic microorganisms in wounds. Through a combination of hydrophilic and hydrophobic sorbents these products can provide clean wounds through a selective sorption and draining effect.

The composite wound healing preparation "Flotoxan" includes highly dispersed hydrophilic silica and hydrophobic polymethylsiloxane in a mixture with a surface-active antimicrobial substance such as ethonium [Ukrainian patent UA 32088 A, Wound healing preparation "Flotoxan" and way of its preparation, Shevchenko Y. M., Gerashchenko Viltsanyuk O. A.]. The preparation has a high antimicrobial activity and dehydrating effect, the ability to absorb and to retain proteins, bacteria and their toxins, metabolites of middle molecular weight, whereby the resorption of the mentioned substances through the wound surface is prevented. Also, due to activation of protease activity by the preparation the content of the wound shows proteolytic properties although the preparation does not contain a component with antimicrobial activity against anaerobic microorganisms.

SUMMARY OF THE INVENTION

The aim of the invention is to eliminate the aforementioned shortcomings by creating a universal hydrophilic-hydrophobic composition having an sorptive and detoxifying effect for the treatment of purulent wounds and other purulo-inflammatory diseases such as chronic purulo-granulomatous inflammation, and purulo-necrotic inflammation. The composition according to this invention may be varied, depending on the phase of wound healing. This may be achieved by varying the dehydrating ability, adding compounds having a wide range of antimicrobial activity, e.g. against aerobic and anaerobic microorganisms. Moreover additional compounds may be added which exhibit necrolytic effects on non-vital tissues, enhance the regenerative effect on the young tissue and/or provide a local anesthetic effect. By using the composition according to the present invention, a more effective treatment of wounds of different nature in various stages of wound healing may be achieved, which include: exudating wounds, chronic pressure ulcers, venous leg ulcers, diabetic/neuropathic ulcers, fungating, cancerous or malignant lesions and wounds with necrotic tissue.

Thus, the present invention provides in a first aspect a composition in powder form comprising highly dispersed silica particles, polymethylsiloxane particles, and one or both of a cationic surfactant and an antimicrobial substance, wherein at least one of the following conditions is fulfilled:
a) at least 25% by weight of the cationic surfactant is present in primary polymethylsiloxane particles carrying the cationic surfactant on their surface and/or in agglomerates of these primary particles; and b) at least 25% by weight, of the antimicrobial substance is present in primary highly dispersed silica particles carrying the antimicrobial substance on their surface and/or in agglomerates of these primary particles.

In a second aspect, the present invention provides a composition in powder form comprising:
21.0 to 75.0 wt. % of highly dispersed silica;
16.0 to 70.0 wt. % of polymethylsiloxane;
at least one of a cationic surfactant in an amount of 0.2 to 4.0 wt. % and an antimicrobial substance in an amount of 0.5 to 10 wt. %;
and further at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

Furthermore, the present invention provides in a third aspect a method of producing a composition in powder form comprising the following steps (a) to (c):
(a) providing highly dispersed silica particles, polymethylsiloxane particles, and one or both of a cationic surfactant and an antimicrobial substance;
(b) carrying out at least one of the following steps (b1) and (b2):
  (b1) forming primary polymethylsiloxane particles carrying the cationic surfactant on their surface and/or agglomerates of these primary particles,
  (b2) forming primary highly dispersed silica particles carrying the antimicrobial substance on their surface and/or agglomerates of these primary particles using a minor part of the highly dispersed silica particles; and
(c) mixing the major part of the highly dispersed silica particles with the products obtained in step (b).

In a fourth aspect the present invention provides a method of producing a composition in powder form comprising mechanical mixing of:
21.0 to 75.0 wt. % of the highly dispersed silica;
16.0 to 70.0 wt. % of the polymethylsiloxane;
at least one of a cationic surfactant in an amount of 0.2 to 4.0 wt. % and an antimicrobial substance in an amount of 0.5 to 10 wt. %;
and further at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

The present invention also provides a pharmaceutical preparation which is or comprises the composition in powder form according to the first or second aspect of the present invention.

DETAILED DESCRIPTION

Figure 1:
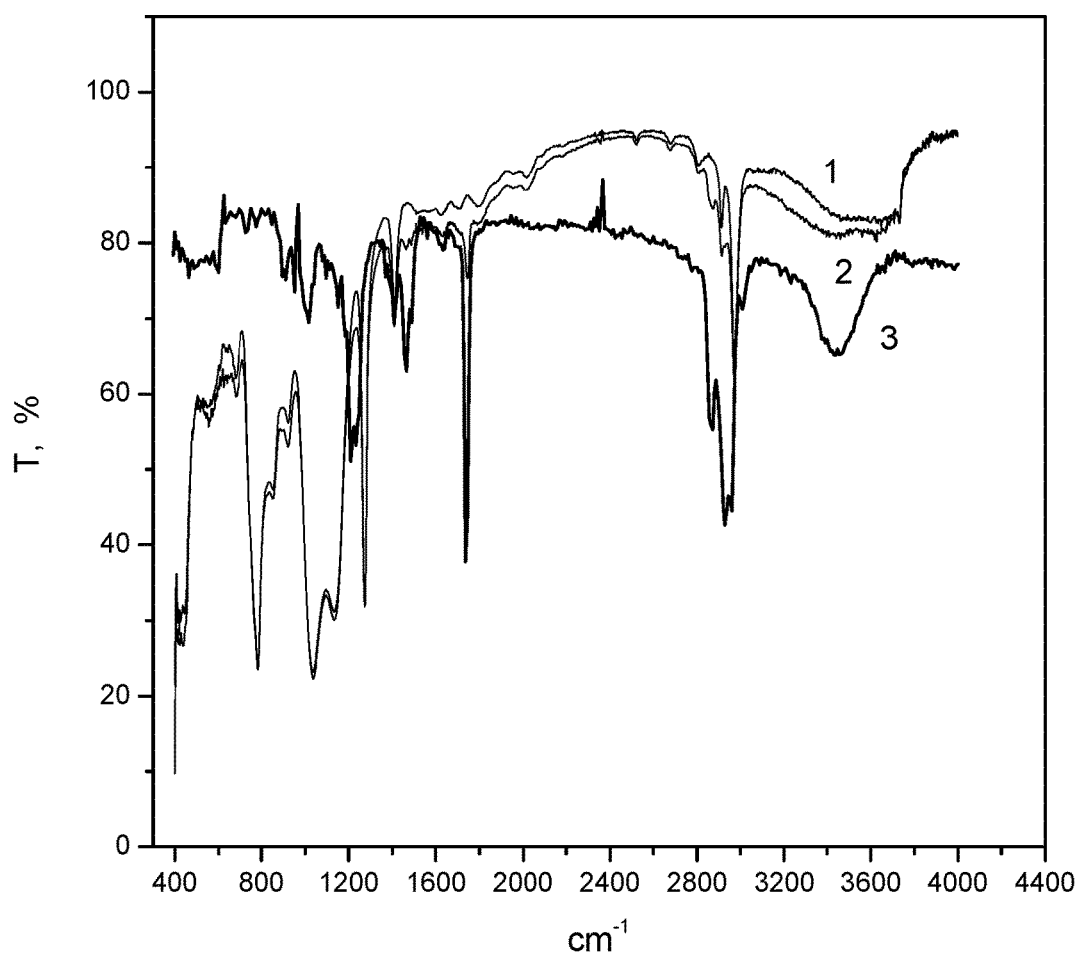
FIG. 1 shows the IR-spectrum of "Polymethylsiloxane+decamethoxin". The top line (line 1) relates to polymethylsiloxane after milling for 1 hour; the middle line (line 2) relates to a mixture of polymethylsiloxane and decamethoxin after milling for 1 hour and the bottom line (line 3) relates to decamethoxin. This spectrum shows that the main part of decamethoxin is immobilized on the polymethylsiloxane surface and only a little amount of the decamethoxine remains in a non-immobilized state.

Thus, the present invention provides in a first aspect a composition in powder form comprising highly dispersed silica particles, polymethylsiloxane particles, and one or both of a cationic surfactant and an antimicrobial substance, wherein at least one of the following conditions is fulfilled:
a) at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles; and
b) at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles.

This means that at least one of a cationic surfactant and an antimicrobial substance must be present in the composition and preferably both of a cationic surfactant and an antimicrobial substance are present in the composition of the present invention. If the cationic surfactant is comprised in the composition and no antimicrobial substance is present, condition a) must be fulfilled, i.e., at least 25% by weight of the cationic surfactant is present in primary polymethylsiloxane particles carrying the cationic surfactant on their surface or in agglomerates of these primary particles. If the antimicrobial substance is comprised in the composition and no cationic surfactant is present, condition b) must be fulfilled, i.e., at least 25% by weight of the antimicrobial substance is present in primary highly dispersed silica particles carrying the antimicrobial substance on their surface or in agglomerates of these primary particles. If both of a cationic surfactant and an antimicrobial substance are present, at least one of conditions a) and b) must be fulfilled and preferably both conditions a) and b) are fulfilled.

Thus, according to a preferred embodiment of the first aspect, the present invention provides a composition in powder form comprising highly dispersed silica particles, polymethylsiloxane particles, a cationic surfactant and an antimicrobial substance, wherein at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles, and at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles. Preferably at least 50% by weight of the cationic surfactant is present in primary polymethylsiloxane particles carrying the cationic surfactant on their surface or in agglomerates of these primary particles, and at least 50% by weight of the antimicrobial substance is present in primary highly dispersed silica particles carrying the antimicrobial substance on their surface or in agglomerates of these primary particles.

In a more preferred embodiment of the first aspect, the present invention provides a composition in powder form comprising highly dispersed silica particles, polymethylsiloxane particles, and one or both of a cationic surfactant and an antimicrobial substance, wherein at least one of the following conditions is fulfilled:

a) at least 25% by weight, preferably 25 to 80% by weight, more preferably 40 to 80% by weight, most preferably 40 to 60% by weight of the cationic surfactant is present in primary polymethylsiloxane particles having the cationic surfactant mechanochemically immobilized onto their surface and/or in agglomerates of these primary particles; and b) at least 25% by weight, preferably 25 to 80% by weight, more preferably 40 to 80% by weight, most preferably 40 to 60% by weight of the antimicrobial substance is present in primary highly dispersed silica particles having the antimicrobial substance mechanochemically immobilized onto the surface of a part of the highly dispersed silica and/or in agglomerates of these primary particles.

This means that at least one of a cationic surfactant and an antimicrobial substance must be present in the composition and preferably both of a cationic surfactant and an antimicrobial substance are present in the composition of the present invention. If the cationic surfactant is comprised in the composition and no antimicrobial substance is present, condition a) must be fulfilled, i.e., at least 25% by weight of the cationic surfactant is present in primary polymethylsiloxane particles having the cationic surfactant mechanochemically immobilized onto their surface or in agglomerates of these primary particles. If the antimicrobial substance is comprised in the composition and no cationic surfactant is present, condition b) must be fulfilled, i.e., at least 25% by weight of the antimicrobial substance is present in primary highly dispersed silica particles having the cationic surfactant mechanochemically immobilized onto their surface or in agglomerates of these primary particles. If both of a cationic surfactant and an antimicrobial substance are present, at least one of conditions a) and b) must be fulfilled and preferably both conditions a) and b) are fulfilled.

Thus, according to an even more preferred embodiment of the first aspect, the present invention provides a composition in powder form comprising highly dispersed silica particles, polymethylsiloxane particles, a cationic surfactant and an antimicrobial substance, wherein at least 25% by weight, preferably 25 to 80% by weight, more preferably 40 to 80% by weight, most preferably 40 to 60% by weight of the cationic surfactant is present in primary polymethylsiloxane particles having the cationic surfactant mechanochemically immobilized onto their surface and/or in agglomerates of these primary particles, and at least 25% by weight, preferably 25 to 80% by weight, more preferably 40 to 80% by weight, most preferably 40 to 60% by weight of the antimicrobial substance is present in primary highly dispersed silica particles having the antimicrobial substance mechanochemically immobilized onto the surface of a part of the highly dispersed silica and/or in agglomerates of these primary particles. Preferably, the part of the highly dispersed silica onto which the antimicrobial substance is mechanochemically immobilized is 5 to 30 wt. %, preferably 10 to 20 wt. %, more preferably 11 to 15 wt. % of the total weight of the highly dispersed silica comprised in the composition. Preferably, at least 50% by weight of the cationic surfactant is mechanochemically immobilized onto the polymethylsiloxane, and at least 50% by weight of the antimicrobial substance is mechanochemically immobilized onto a part of the highly dispersed silica representing 10 to 20 wt. % of the total weight of the highly dispersed silica comprised in the composition.

The composition of the first aspect of the present invention preferably comprises:
  21.0 to 75.0 wt. % of the highly dispersed silica;
  16.0 to 70.0 wt. % of the polymethylsiloxane;
  and at least one of a cationic surfactant in an amount of 0.2 to 4.0 wt. % and an antimicrobial substance in an amount of 0.5 to 10 wt. %;
  based on the total weight of the composition.

More preferably, the composition of the first aspect of the present invention comprises:
  35.0 to 70.0 wt. % of the highly dispersed silica;
  20.0 to 45.0 wt. % of the polymethylsiloxane;
  and at least one of a cationic surfactant in an amount of 0.8 to 2.0 wt. % and an antimicrobial substance in an amount of 1.5 to 8 wt. %;
  based on the total weight of the composition.

The composition of the first aspect of the present invention even more preferably comprises:
  21.0 to 75.0 wt. % of the highly dispersed silica,
  16.0 to 70.0 wt. % of the polymethylsiloxane,
  0.2 to 4.0 wt. % of the cationic surfactant, and
  0.5 to 10 wt. % of the antimicrobial substance,
  based on the total weight of the composition.

Most preferably, the composition of the first aspect of the present invention comprises:
  35.0 to 70.0 wt. % of the highly dispersed silica,
  20.0 to 45.0 wt. % of the polymethylsiloxane,
  0.8 to 2.0 wt. % of the cationic surfactant, and
  1.5 to 8 wt. % of the antimicrobial substance,
  based on the total weight of the composition.

Preferably, the composition of the first aspect of the present invention as described above further comprises at least one additional agent selected from the group consisting of substances with tissue growth activity, lidocaine, phenothiazine derivatives, proteolytic enzymes, and combinations thereof. More preferably, the composition comprises, in addition to highly dispersed silica, polymethylsiloxane, a cationic surfactant and an antimicrobial substance, at least one of the following agents:
  0.01 to 10.0 wt. % of at least one substance with tissue growth activity,
  0.01 to 5.0 wt. % lidocaine,
  0.01 to 5.0 wt. % of at least one phenothiazine derivative, and
  0.01 to 3.0 wt. % of at least one proteolytic enzyme,
  based on the total weight of the composition.

In a second aspect, the present invention provides a composition in powder form comprising:
  21.0 to 75.0 wt. % of highly dispersed silica;
  16.0 to 70.0 wt. % of polymethylsiloxane;
  at least one of a cationic surfactant in an amount of 0.2 to 4.0 wt. % and an antimicrobial substance in an amount of 0.5 to 10 wt. %;
  and further at least one of the following agents:
  0.01 to 10.0 wt. % of at least one substance with tissue growth activity,
  0.01 to 5.0 wt. % lidocaine, 0.01 to 5.0 wt. % of at least one phenothiazine derivative, and
0.01 to 3.0 wt. % of at least one proteolytic enzyme,
based on the total weight of the composition.

Preferably, the composition according to the second aspect of the present invention comprises:
35.0 to 75.0 wt. % of highly dispersed silica;
20.0 to 45.0 wt. % of polymethylsiloxane;
at least one of a cationic surfactant in an amount of 0.8 to 2.0 wt. % and an antimicrobial substance in an amount of 1.5 to 8 wt. %;
and further at least one of the following agents:
0.1 to 5.0 wt. % of at least one substance with tissue growth activity,
0.1 to 3.0 wt. % of lidocaine,
0.1 to 3.0 wt. % of at least one phenothiazine derivative, and
0.1 to 2.0 wt. % of at least one proteolytic enzyme,
based on the total weight of the composition.

This means that at least one of a cationic surfactant and an antimicrobial substance must be present in the composition and preferably both of a cationic surfactant and an antimicrobial substance are present in the composition according to the second aspect of the present invention. Furthermore, the second aspect of the present invention encompasses (i) a composition which comprises a cationic surfactant and does not comprise an antimicrobial substance; and (ii) a composition which comprises an antimicrobial substance and does not comprise a cationic surfactant.

The composition of the second aspect of the present invention even more preferably comprises provides a composition in powder form comprising:
21.0 to 75.0 wt. % of highly dispersed silica;
16.0 to 70.0 wt. % of polymethylsiloxane;
0.2 to 4.0 wt. % of a cationic surfactant;
0.5 to 10 wt. % of an antimicrobial substance;
and at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

Most preferably, the composition according to the second aspect of the present invention comprises:
35.0 to 75.0 wt. % of highly dispersed silica;
20.0 to 45.0 wt. % of polymethylsiloxane;
0.8 to 2.0 wt. % of a cationic surfactant;
1.5 to 8 wt. % of an antimicrobial substance;
and at least one of the following agents:
0.1 to 5.0 wt. % of at least one substance with tissue growth activity,
0.1 to 3.0 wt. % of lidocaine,
0.1 to 3.0 wt. % of at least one phenothiazine derivative, and
0.1 to 2.0 wt. % of at least one proteolytic enzyme,
based on the total weight of the composition.

In the composition of the first and second aspects of the present invention the sorbents, i.e. the sum of the highly dispersed silica and the polymethylsiloxane, preferably represent 65 to 97 wt. %, more preferably 80 to 95 wt. % of the total weight of the composition.

In the composition of the first and second aspects of the present invention the highly dispersed silica is preferably selected from the group consisting of fumed silica, precipitated silica, colloidal anhydrous silica, silicagel, Syloid®, Aerosil®, and combinations thereof.

The cationic surfactant used in the first and second aspects of the present invention is preferably selected from mono- or bis-quaternary ammonium compounds. More preferably, the cationic surfactant is selected from the group consisting of ethonium, decamethoxine, octenidine dihydrochloride, benzalkonium chloride, myramistine, and combinations thereof.

The antimicrobial substance used in the first and second aspects of the present invention is preferably selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof.

The present invention provides in a fifth aspect a composition in powder form comprising polymethylsiloxane particles and a cationic surfactant, wherein at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles.

Preferably at least 50% by weight of the cationic surfactant is present in primary polymethylsiloxane particles carrying the cationic surfactant on their surface or in agglomerates of these primary particles.

In a preferred embodiment of the fifth aspect, the present invention provides a composition in powder form comprising polymethylsiloxane particles and a cationic surfactant, wherein at least 25% by weight, preferably 25 to 80% by weight, more preferably 40 to 80% by weight, most preferably 40 to 60% by weight of the cationic surfactant is present in primary polymethylsiloxane particles having the cationic surfactant mechanochemically immobilized onto their surface and/or in agglomerates of these primary particles. Preferably, at least 50% by weight of the cationic surfactant is mechanochemically immobilized onto the polymethylsiloxane.

The composition of the fifth aspect of the present invention preferably comprises:
90.0 to 99.8 wt. % of the polymethylsiloxane, and
0.2 to 10 wt. % of the cationic surfactant,
based on the total weight of the composition.

More preferably, the composition of the fifth aspect of the present invention comprises:
95.0 to 99.0 wt. % of the polymethylsiloxane, and
1 to 5.0 wt. % of the cationic surfactant,
based on the total weight of the composition.

Preferably, the composition of the fifth aspect of the present invention does not contain highly dispersed silica and/or an antimicrobial substance different from the cationic surfactant. More preferably, the composition of the fifth aspect of the present invention consists of polymethylsiloxane particles and a cationic surfactant.

The cationic surfactant used in the fifth aspects of the present invention is preferably selected from mono- or bis-quaternary ammonium compounds. More preferably, the cationic surfactant is selected from the group consisting of ethonium, decamethoxine, octenidine dihydrochloride, benzalkonium chloride, myramistine, and combinations thereof.

The present invention provides in a sixth aspect a composition in powder form comprising highly dispersed silica particles and an antimicrobial substance, wherein at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles. Preferably at least 50% by weight of the antimicrobial substance is present in primary highly dispersed silica particles carrying the antimicrobial substance on their surface or in agglomerates of these primary particles.

In a more preferred embodiment of the sixth aspect, the present invention provides a composition in powder form comprising highly dispersed silica particles and an antimicrobial substance, wherein at least 25% by weight, preferably 25 to 80% by weight, more preferably 40 to 80% by weight, most preferably 40 to 60% by weight of the antimicrobial substance is present in primary highly dispersed silica particles having the antimicrobial substance mechanochemically immobilized onto the surface of a part of the highly dispersed silica and/or in agglomerates of these primary particles. Preferably, the part of the highly dispersed silica onto which the antimicrobial substance is mechanochemically immobilized is 5 to 30 wt. %, preferably 10 to 20 wt. %, more preferably 11 to 15 wt. % of the total weight of the highly dispersed silica comprised in the composition. Preferably, at least 50% by weight of the antimicrobial substance is mechanochemically immobilized onto a part of the highly dispersed silica representing 10 to 20 wt. % of the total weight of the highly dispersed silica comprised in the composition.

The composition of the sixth aspect of the present invention preferably comprises:
  80.0 to 99.5 wt. % of the highly dispersed silica, and
  0.5 to 20 wt. % of the antimicrobial substance,
  based on the total weight of the composition.
More preferably, the composition of the sixth aspect of the present invention comprises:
  85 to 98.5 wt. % of the highly dispersed silica, and
  1.5 to 15 wt. % of the antimicrobial substance,
  based on the total weight of the composition.

Preferably, the composition of the sixth aspect of the present invention does not contain polymethylsiloxane and/or a cationic surfactant. More preferably, the composition of the sixth aspect of the present invention consists of highly dispersed silica particles and an antimicrobial substance.

Preferably, the composition of the fifth or sixth aspect of the present invention as described above further comprises at least one additional agent selected from the group consisting of substances with tissue growth activity, lidocaine, phenothiazine derivatives, proteolytic enzymes, and combinations thereof. More preferably, the composition comprises, in addition to highly dispersed silica, polymethylsiloxane, a cationic surfactant and an antimicrobial substance, at least one of the following agents:
  0.01 to 10.0 wt. % of at least one substance with tissue growth activity,
  0.01 to 5.0 wt. % lidocaine,
  0.01 to 5.0 wt. % of at least one phenothiazine derivative, and
  0.01 to 3.0 wt. % of at least one proteolytic enzyme,
  based on the total weight of the composition.

In the composition of the sixth aspect of the present invention the highly dispersed silica is preferably selected from the group consisting of fumed silica, precipitated silica, colloidal anhydrous silica, silicagel, Syloid®, Aerosil®, and combinations thereof.

The antimicrobial substance used in the sixth aspect of the present invention is preferably selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof.

The method of preparing the composition of the first second, fifth and sixth aspects of the present invention is not particularly limited.

In a third aspect, the present invention provides a method of producing a composition in powder form comprising the following steps (a) to (c):
(a) providing highly dispersed silica particles, polymethylsiloxane particles, and one or both of a cationic surfactant and an antimicrobial substance;
(b) carrying out at least one of the following steps (b1) and (b2):
  (b1) forming primary polymethylsiloxane particles carrying the cationic surfactant on their surface and/or in agglomerates of these primary particles,
  (b2) forming primary highly dispersed silica particles carrying the antimicrobial substance on their surface and/or in agglomerates of these primary particles using a minor part of the highly dispersed silica particles; and
(c) mixing the major part of the highly dispersed silica particles with the products obtained in step (b).

This means that at least one of a cationic surfactant and an antimicrobial substance must be provided in step (a) and preferably both of a cationic surfactant and an antimicrobial substance are provided in step (a). If the cationic surfactant is provided and no antimicrobial substance is provided, step (b1) must be carried out, i.e., primary polymethylsiloxane particles carrying the cationic surfactant on their surface and/or in agglomerates of these primary particles are formed, and all of the highly dispersed silica particles are employed in step (c). If the antimicrobial substance is provided and no cationic surfactant is provided, step (b2) must be carried out, i.e., primary highly dispersed silica particles carrying the antimicrobial substance on their surface and/or in agglomerates of these primary particles using a minor part of the highly dispersed silica particles are formed.

It is preferred that both of a cationic surfactant and an antimicrobial substance are provided in step (a). In this case at least one of steps (b1) and (b2) must be carried out. If step (b1), but not step (b2), is carried out, a minor part of the highly dispersed silica particles may be mixed with the antimicrobial substance in a step (b2') and the major part of the highly dispersed silica particles is mixed with the products obtained in steps (b1) and (b2') in step (c). Alternatively, all of the highly dispersed silica particles are mixed with the products obtained in step (b1) and the antimicrobial substance in step (c). If step (b2), but not step (b1), is carried out, the polymethylsiloxane particles may be mixed with the cationic surfactant in a step (b1') and the major part of the highly dispersed silica particles is mixed with the products obtained in steps (b1') and (b2) in step (c). Alternatively, the major part of the highly dispersed silica particles is mixed with the product obtained in step (b2), the polymethylsiloxane particles and the cationic surfactant in step (c). Preferably both of steps (b1) and (b2) are carried out.

Thus, according to a preferred embodiment of the third aspect, the present invention provides a method of producing a composition in powder form comprising the following steps (a) to (c):
(a) providing highly dispersed silica particles, polymethylsiloxane particles, a cationic surfactant, and an antimicrobial substance;

(b) carrying out the following steps (b1) and (b2):
   (b1) forming primary polymethylsiloxane particles carrying the cationic surfactant on their surface and/or in agglomerates of these primary particles,
   (b2) forming primary highly dispersed silica particles carrying the antimicrobial substance on their surface and/or in agglomerates of these primary particles using a minor part of the highly dispersed silica particles; and
(c) mixing the major part of the highly dispersed silica particles with the products obtained in step (b).

A skilled person will appreciate that in the method according to the third aspect of the present invention, step (a) is carried out before step (b) and step (c) is carried out after step (b), while steps (b1) and (b2) can be carried out consecutively in arbitrary order or simultaneously. In the resulting composition at least one of the following conditions is fulfilled:

a) at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles, and b) at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles.

It is preferred that in the resulting composition at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles, and at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles. Preferably at least 50% by weight of the cationic surfactant is present in primary polymethylsiloxane particles carrying the cationic surfactant on their surface or in agglomerates of these primary particles, and at least 50% by weight of the antimicrobial substance is present in primary highly dispersed silica particles carrying the antimicrobial substance on their surface or in agglomerates of these primary particles.

In the method according to the third aspect, the major part of the highly dispersed silica particles employed in step (c) preferably represents 70 to 95 wt. %, more preferably 80 to 90 wt. %, even more preferably 85 to 89 wt. % of the total weight of the highly dispersed silica comprised in the composition. Preferably, the major part of the highly dispersed silica particles employed in step (c) represents 70 to 95 wt. %, preferably 80 to 90 wt. %, more preferably 85 to 89 wt. % of the total weight of the highly dispersed silica comprised in the composition and the remaining highly dispersed silica particles form the minor part of the highly dispersed silica particles employed in step (b2).

Preferably, the composition obtainable by the above method comprises:
   21.0 to 75.0 wt. % of the highly dispersed silica;
   16.0 to 70.0 wt. % of the polymethylsiloxane;
   and at least one of a cationic surfactant in an amount of 0.2 to 4.0 wt. %, and an antimicrobial substance in an amount of 0.5 to 10 wt. %;
   based on the total weight of the composition.

More preferably, the composition obtainable by the above method comprises:
   35.0 to 70.0 wt. % of the highly dispersed silica;
   20.0 to 45.0 wt. % of the polymethylsiloxane;
   and at least one of a cationic surfactant in an amount of 0.8 to 2.0 wt. %, and an antimicrobial substance in an amount of 1.5 to 8 wt. %;
   based on the total weight of the composition.

Even more preferably, the composition obtainable by the above method comprises:
   21.0 to 75.0 wt. % of the highly dispersed silica,
   16.0 to 70.0 wt. % of the polymethylsiloxane,
   0.2 to 4.0 wt. % of the cationic surfactant, and
   0.5 to 10 wt. % of the antimicrobial substance,
   based on the total weight of the composition.

Most preferably, the composition obtainable by the above method comprises:
   35.0 to 70.0 wt. % of the highly dispersed silica,
   20.0 to 45.0 wt. % of the polymethylsiloxane,
   0.8 to 2.0 wt. % of the cationic surfactant, and
   1.5 to 8 wt. % of the antimicrobial substance,
   based on the total weight of the composition.

It is further preferred, that the composition obtainable by the above method further comprises at least one additional agent selected from the group consisting of substances with tissue growth activity, lidocaine, phenothiazine derivatives, proteolytic enzymes, and combinations thereof.

More preferably, the composition obtainable by the above method further comprises at least one of the following agents:
   0.01 to 10.0 wt. % of at least one substance with tissue growth activity,
   0.01 to 5.0 wt. % lidocaine,
   0.01 to 5.0 wt. % of at least one phenothiazine derivative, and
   0.01 to 3.0 wt. % of at least one proteolytic enzyme,
   based on the total weight of the composition.

In the above described method according to the third aspect, it is preferred, that the primary particles of the highly dispersed silica formed in step (b2) carry the antimicrobial substance and at least one further substance selected from the group consisting of compounds having tissue growth activity, lidocaine, and phenothiazine derivatives on their surface. Even more preferably, the primary particles of the highly dispersed silica carry the antimicrobial substance and at least one further substance selected from the group consisting of salts of zinc, methyluracil, lidocaine, and chlorpromazine on their surface.

In the above described method of the third aspect of the present invention, it is preferred, that in step (c) the major part of the highly dispersed silica is mixed with the products obtained from step (b) and at least one component selected from zinc oxide, and proteolytic enzymes.

In the above method, the formation of the primary particles or their agglomerates in steps (b1) and (b2) is preferably achieved by milling the respective components. Preferably, the milling is carried out using a ball mill or a vibrational mill. When a ball mill having a drum volume of 2 liters is used in step (b1), preferably the time of milling is 30-60 minutes, and the speed of rotation of the drum is 0.5-2 rev/sec. When a ball mill having a drum volume of 2 liters is used in step (b2), preferably the time of milling is 20-60 minutes, and the speed of rotation of the drum is 0.5-2 rev/sec. For ball mills having a higher drum volume of, e.g., 5, 10, or 50 liters, the time of milling may be higher, e.g., 60 to 120 min. The ball mill immobilization in steps (b1) and/or (b2) can be intensified by adding ethanol or water in an amount of 10 to 60 wt. %, more preferably 25 to 50 wt. % based on the weight of the highly dispersed silica or the polymethylsiloxane, respectively, into the drum before the milling process and drying either the products of steps (b1) and (b2), or drying the mixed product of step (c).

In the above described method, step (c) is preferably carried out using a hermetically sealed high-speed mixer with vane. The mixing time should preferably be sufficient to obtain a finely dispersed, visually homogeneous powder preparation.

In a preferred embodiment of the above described method according to the third aspect of the present invention the cationic surfactant is mechanochemically immobilized onto the polymethylsiloxane particles in step (b1); and the antimicrobial substance and optionally at least one further substance selected from the group consisting of compounds having tissue growth activity, lidocaine, and phenothiazine derivatives are mechanochemically immobilized onto the highly dispersed silica particles in step (b2).

In the above described method according to the third aspect of the present invention the minor part of the highly dispersed silica particles employed in step (b2) preferably represents 5 to 30 wt. %, more preferably 10 to 20 wt. %, most preferably 11 to 15 wt. % of the total weight of the highly dispersed silica comprised in the composition. Preferably, the remaining highly dispersed silica particles form the major part of the highly dispersed silica particles employed in step (c), which preferably represents 70 to 95 wt. %, more preferably 80 to 90 wt. %, most preferably 85 to 89 wt. % of the total weight of the highly dispersed silica comprised in the composition.

In a seventh aspect, the present invention provides a method of producing a composition in powder form comprising the following steps:
(a) providing polymethylsiloxane particles and a cationic surfactant;
(b1) forming primary polymethylsiloxane particles carrying the cationic surfactant on their surface and/or in agglomerates of these primary particles.

In the resulting composition at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles. Preferably at least 50% by weight of the cationic surfactant is present in primary polymethylsiloxane particles carrying the cationic surfactant on their surface or in agglomerates of these primary particles.

Preferably, the composition obtainable by the above method comprises:
90.0 to 99.8 wt. % of the polymethylsiloxane, and
0.2 to 10 wt. % of the cationic surfactant,
based on the total weight of the composition.

More preferably, the composition obtainable by the above method comprises:
95.0 to 99.0 wt. % of the polymethylsiloxane, and
1 to 5.0 wt. % of the cationic surfactant,
based on the total weight of the composition.

In a preferred embodiment of the above described method according to the seventh aspect of the present invention the cationic surfactant is mechanochemically immobilized onto the polymethylsiloxane particles in step (b1).

The present invention further provides a composition in powder form obtainable by the above described methods of the seventh aspect of the present invention. It is particularly preferable, that the composition in powder form according to the fifth aspect of the present invention is obtainable by the method of the seventh aspect of the present invention.

In an eighth aspect, the present invention provides a method of producing a composition in powder form comprising the following steps:
(a) providing highly dispersed silica particles and an antimicrobial substance;
(b2) forming primary highly dispersed silica particles carrying the antimicrobial substance on their surface and/or in agglomerates of these primary particles using a minor part of the highly dispersed silica particles; and
(c) mixing the major part of the highly dispersed silica particles with the products obtained in step (b2).

In the resulting composition at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles. Preferably, at least 50% by weight of the antimicrobial substance is present in primary highly dispersed silica particles carrying the antimicrobial substance on their surface or in agglomerates of these primary particles.

In the method according to the eighth aspect, the major part of the highly dispersed silica particles employed in step (c) preferably represents 70 to 95 wt. %, more preferably 80 to 90 wt. %, even more preferably 85 to 89 wt. % of the total weight of the highly dispersed silica comprised in the composition. Preferably, the major part of the highly dispersed silica particles employed in step (c) represents 70 to 95 wt. %, preferably 80 to 90 wt. %, more preferably 85 to 89 wt. % of the total weight of the highly dispersed silica comprised in the composition and the remaining highly dispersed silica particles form the minor part of the highly dispersed silica particles employed in step (b2).

Preferably, the composition obtainable by the above method comprises:
80.0 to 99.5 wt. % of the highly dispersed silica, and
0.5 to 20 wt. % of the antimicrobial substance,
based on the total weight of the composition.

More preferably, the composition obtainable by the above method comprises:
85 to 98.5 wt. % of the highly dispersed silica, and
1.5 to 15 wt. % of the antimicrobial substance,
based on the total weight of the composition.

It is further preferred, that the composition obtainable by the above method further comprises at least one additional agent selected from the group consisting of substances with tissue growth activity, lidocaine, phenothiazine derivatives, proteolytic enzymes, and combinations thereof.

More preferably, the composition obtainable by the above method of the seventh or eighth aspect further comprises at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

In the above described method according to the eighth aspect, it is preferred, that the primary particles of the highly dispersed silica formed in step (b2) carry the antimicrobial substance and at least one further substance selected from the group consisting of compounds having tissue growth activity, lidocaine, and phenothiazine derivatives on their surface. Even more preferably, the primary particles of the highly dispersed silica carry the antimicrobial substance and at least one further substance selected from the group consisting of salts of zinc, methyluracil, lidocaine, and chlorpromazine on their surface.

In the above described method of the eighth aspect of the present invention, it is preferred, that in step (c) the major part of the highly dispersed silica is mixed with the products obtained from step (b2) and at least one component selected from zinc oxide, and proteolytic enzymes.

The present invention further provides a composition in powder form obtainable by the above described methods of the eighth aspect of the present invention. It is particularly preferable, that the composition in powder form according to the sixth aspect of the present invention is obtainable by the method of the eighth aspect of the present invention.

In the above method according to the seventh and eighth aspects, the formation of the primary particles or their agglomerates in steps (b1) and (b2) is preferably achieved by milling the respective components. Preferably, the milling is carried out using a ball mill or a vibrational mill. When a ball mill having a drum volume of 2 liters is used in step (b1), preferably the time of milling is 30-60 minutes, and the speed of rotation of the drum is 0.5-2 rev/sec. When a ball mill having a drum volume of 2 liters is used in step (b2), preferably the time of milling is 20-60 minutes, and the speed of rotation of the drum is 0.5-2 rev/sec. For ball mills having a higher drum volume of, e.g., 5, 10, or 50 liters, the time of milling may be higher, e.g., 60 to 120 min. The ball mill immobilization in steps (b1) and/or (b2) can be intensified by adding ethanol or water in an amount of 10 to 60 wt. %, more preferably 25 to 50 wt. % based on the weight of the highly dispersed silica or the polymethylsiloxane, respectively, into the drum before the milling process and drying either the products of steps (b1) and (b2), or drying the mixed product of step (c).

In the above described method according to the eighth, step (c) is preferably carried out using a hermetically sealed high-speed mixer with vane. The mixing time should preferably be sufficient to obtain a finely dispersed, visually homogeneous powder preparation.

In a preferred embodiment of the above described method according to the eighth aspect of the present invention the antimicrobial substance and optionally at least one further substance selected from the group consisting of compounds having tissue growth activity, lidocaine, and phenothiazine derivatives are mechanochemically immobilized onto the highly dispersed silica particles in step (b2).

In the above described method according to the eighth aspect of the present invention the minor part of the highly dispersed silica particles employed in step (b2) preferably represents 5 to 30 wt. %, more preferably 10 to 20 wt. %, most preferably 11 to 15 wt. % of the total weight of the highly dispersed silica comprised in the composition. Preferably, the remaining highly dispersed silica particles form the major part of the highly dispersed silica particles employed in step (c), which preferably represents 70 to 95 wt. %, more preferably 80 to 90 wt. %, most preferably 85 to 89 wt. % of the total weight of the highly dispersed silica comprised in the composition.

The present invention further provides a composition in powder form obtainable by the above described methods of the eighth aspect of the present invention. It is particularly preferable, that the composition in powder form according to the sixth aspect of the present invention is obtainable by the method of the eighth aspect of the present invention.

The present invention also provides the following kits:
a kit comprising separately the composition according to the fifth aspect and highly dispersed silica particles;
a kit comprising separately the composition according to the sixth aspect and polymethylsiloxane particles;
a kit comprising separately the composition according to the fifth aspect and the composition according to the sixth aspect.

In a fourth aspect, the present invention provides a method of producing a composition in powder form comprising mechanical mixing of:
21.0 to 75.0 wt. % of the highly dispersed silica;
16.0 to 70.0 wt. % of the polymethylsiloxane;
at least one of a cationic surfactant in an amount of 0.2 to 4.0 wt. % and an antimicrobial substance in an amount of 0.5 to 10 wt. %;
and further at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme, based on the total weight of the composition.

This means that at least one of a cationic surfactant and an antimicrobial substance must be employed in the method and preferably both of a cationic surfactant and an antimicrobial substance are employed in the method according to the fourth aspect of the present invention.

In a preferred embodiment, the fourth aspect of the present invention provides a method of producing a composition in powder form comprising mechanical mixing of:
21.0 to 75.0 wt. % of the highly dispersed silica;
16.0 to 70.0 wt. % of the polymethylsiloxane;
0.2 to 4.0 wt. % of the cationic surfactant;
0.5 to 10 wt. % of the antimicrobial substance;
and at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme, based on the total weight of the composition.

The mixing time in the method of the fourth aspect of the present invention should preferably be sufficient to obtain a finely dispersed, visually homogeneous powder preparation. The mixing is preferably carried out using a hermetically sealed high-speed mixer with vane. The mixing time when using a hermetically sealed high-speed mixer with vane is preferably 10 to 30 min, more preferably 15 to 20 min.

In a preferred embodiment of the above described method according to the fourth aspect of the present invention, ethanol or water in an amount of 10 to 60 wt. %, more preferably 25 to 50 wt. % based on sum of the weight of the highly dispersed silica and the polymethylsiloxane (i.e., the sorbents) is added, during mixing, and the composition is dried after mixing. More preferably the ethanol or water is gradually added during mixing. In this preferred embodiment, the mixing is preferably carried out using a hermetically sealed high-speed mixer with vane. The mixing time when using a hermetically sealed high-speed mixer with vane is preferably 0.25 to 5.0 hours, more preferably 1 to 4 hours. The use of ethanol or water during the mixing process provides the advantage that the cationic surfactant, the antimicrobial substance and at least one of the agents selected from the group consisting of substances with tissue growth activity, lidocaine, phenothiazine derivatives, and proteolytic enzymes are mechanochemically immobilized onto the sorbents highly dispersed silica and the polymethylsiloxane. Thus, the immobilized substances are present on the surface of the highly dispersed silica particles and the polymethylsiloxane particles and can more readily provide their effects.

In the above described methods of preparing the composition of the third and fourth aspects of the present invention it is preferred that the sum of the highly dispersed silica and the polymethylsiloxane represents 65 to 97 wt. %, more preferably 80 to 95 wt. % of the total weight of the composition.

In the above described methods of preparing the composition of the third and fourth aspects of the present invention it is preferred that the highly dispersed silica is selected from the group consisting of fumed silica, precipitated silica, colloidal anhydrous silica, silicagel, Syloid, Aerosil, and combinations thereof.

Furthermore, it is preferred in the above described methods of preparing the composition of the third and fourth aspects of the present invention that the cationic surfactant is selected from mono- or bis-quaternary ammonium compounds. More preferably, the cationic surfactant is selected from the group consisting of ethonium, decamethoxine, octenidine dihydrochloride, benzalkonium chloride, myramistine, and combinations thereof.

In the above described methods of preparing the composition of the third and fourth aspects of the present invention it is preferred that the antimicrobial substance is selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof.

The present invention further provides a composition in powder form obtainable by the above described methods of the third aspect of the present invention. It is particularly preferable, that the composition in powder form according to the first aspect of the present invention is obtainable by the method of the third aspect of the present invention.

The present invention also provides a composition in powder form obtainable by the above described methods of the fourth aspect of the present invention. It is particularly preferable, that the composition in powder form according to the second aspect of the present invention is obtainable by the method of the fourth aspect of the present invention.

The present invention also provides a pharmaceutical preparation which is or comprises the composition in powder form according to the first or second aspect of the present invention or the composition in powder form obtainable by any of the above described methods of preparing the composition of the third and fourth aspects of the present invention. Thus, the pharmaceutical preparation can be the composition in powder form according to the present invention.

Alternatively, the pharmaceutical preparation may comprise in addition to the composition in powder form according to the present invention further additives. The pharmaceutical preparation is preferably in the form of a powder, a suspension, a gel, an ointment, drops, a suppository, or a tablet.

The present invention also provides a medical article selected from the group consisting of a dressing, packets, or capsules, comprising the pharmaceutical preparation of the present invention.

The composition or the pharmaceutical preparation of the present invention and, preferably, the composition according to the first and second aspects of the present invention can be used in the treatment of purulent wounds and necrotic wounds. More specifically, the composition or the pharmaceutical preparation can be used in the treatment of infected burn surfaces, putrid necrotizing phlegmons and noma in the maxillofacial region, wounds during a larynx or laryngopharynx resection after a cancer surgery, inflammatory diseases of the throat, mouth cavity and/or teeth, pharyngitis, tonsillitis, gingivitis and stomatitis, periodontitis, dental application and ultraphoresis, diseases of the rectum, the large intestine and organs of abdominal cavity, peritonitis, intra-abdominal and pancreatogenic abscesses, complications after pancreatonecrosis, extraperitoneal phlegmons, inflammatory diseases of the uterus and uterine adnexa, urinary bladder, pleura, bones, and other visceral organs, osteomyelitis, urethritis caused by gonococci, trichomonases and other infections, diseases in the front part of the eyes, a fistular in traumatic surgery, food intoxication, acute intestinal obstruction and intoxications by a virus, wounds and impetiginous diseases of the skin, acne, folliculitis and sycosis in the face and/or diseases provoked by irrational application of cosmetics, hemorrhoids, proctitis, anorectal abscesses, anal fissures, wounds after gynecological surgeries, non-specific trichomonal and fungal colpitis, vaginitis, vulvitis, metritis, parametritis, salpingitis, infectious diarrhea, infections caused by *staphylococcus aureus*, methicillin-resistant *staphylococcus aureus* (MRSA), multi-resistant gram-negative bacteria, enterobacteriaceae, and non-fermenting bacteria.

The particle size of the composition of the present invention is preferably 10 to 2,000 nm, more preferably 50 to 1,000 nm, even more preferably 100 to 500 nm. If the composition contains agglomerates, this particle size refers to the size of the primary particles which form the agglomerates. The size of the agglomerates can be in the range of from 2 μm to 500 μm, preferably 5 μm to 250 μm, more preferably 20 to 100 μm. In accordance with the present invention, an agglomerate is a cluster of primary particles held together by weak physical interactions.

The total water content of the composition of the present invention is preferably no higher than 3 wt. %, more preferably no higher than 1 wt.-%, most preferably less than 0.5 wt. %, based on the total weight of the composition.

In the present invention highly dispersed silica ($SiO_2$) is used, which is approved for clinical use as a medicine, as well as an excipient in many preparations [Blitz J. P. and Gun'ko V. M. (eds.) Surface Chemistry in Biomedical and Environmental Science, Springer, 2006, p. 191-204]. Highly dispersed silica is described in U.S. ("Silicon Dioxide"), British and European Pharmacopoeia ("Silica, Colloidal Anhydrous"). Highly dispersed silica in accordance with the present invention includes fumed silica, precipitated silica, colloidal anhydrous silica, silicagel, Syloid® Aerosil®, or other types of porous or non-porous highly dispersed silica. Preferably, the highly dispersed silica is fumed silica, colloidal anhydrous silica, or silicagel. The highly dispersed silica is preferably comprised in the composition of the present invention in an amount of 21.0 to 75.0% by weight, preferably 35.0 to 70.0% by weight, based on the total weight of the composition. The particle size of the highly dispersed silica to be used in the present invention is preferably 2 to 200 nm, more preferably 4 to 150 nm, even more preferably 5 to 50 nm, most preferably 5 to 20 nm. Preferably, the particle size of the highly dispersed silica is not more than 100 nm. The water content of the highly dispersed silica to be used in the present invention is preferably no higher than 3 wt. %, more preferably no higher than 1 wt. %, most preferably less than 0.5 wt. %, based on the total weight of the highly dispersed silica.

Highly dispersed silica can be obtained by high temperature hydrolysis of silicone tetrachloride $SiCl_4$ according to the following reaction scheme:

$$SiCl_4 + 2H_2O \rightarrow SiO_2 + 4HCl$$

The product is usually characterized by a high chemical purity, i.e. the content of $SiO_2$ is not less than 99.9%. The surface area of highly dispersed silica depends on the conditions of synthesis and can range from 150 up to 380 $m^2/gm$.

For preparation of a medical sorbent such as the composition of the present invention, preferably fumed silica is used with a surface area of 300±30 $m^2/gm$.

In the fumed silica the primary spherical nonporous particles usually have a particle size 5 to 20 nm and may be represented by a 3D polymer $(SiO_2)_n$ where $n=10^4-10^5$ in which the atoms of silica and oxygen are linked by a siloxane bond ≡Si—O—Si≡ and the Si atoms show tetrahedral coordination, with 4 oxygen atoms surrounding a central Si atom. Due to hydrogen bonding, electrostatic and Van der Waals forces and with the help of adsorbed molecules of water the primary particles are united into aggregates having a size of about 100 to 200 nm which in turn form aggregates having a particle size of more than 1 μm.

The highly dispersed silica obtained by the above process is an amorphous solid, i.e. it does not have a crystal structure of long-range order. The surface of the highly dispersed silica is covered with hydroxyl groups as shown below, which define the properties of silica as an enterosorbent, i.e. high hydrophilicity, protein-sorption activity and the ability to adsorb microorganisms.

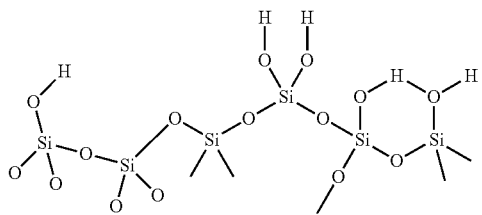

Nowadays the worldwide main producer of highly dispersed silica such as for medical application, is Evonik Industries.

Polymethylsiloxane to be used in the present invention is a finely crushed hydrophobic powder having the general formula $(CH_3SiO_{1.5})_\infty$. Polymethylsiloxane is a xerogel of methylsilicic acid. Polymethylsiloxane is thus different from polydimethylsiloxane (PDMS). Particles of polymethylsiloxane are porous. The specific surface area of the polymethylsiloxane is preferably 100 to 1,000 $m^2/g$, more preferably 300 to 700 $m^2/g$, most preferably 400 to 600 $m^2/g$. The specific surface area of the polymethylsiloxane can be measured by the BET method using nitrogen as adsorbate gas. It is approved for use in medical practice as a matrix for the immobilization of preparations [Shevchenko Y. M., Slinyakova I. B., Yashina N. I., "New bio silica organic porous sorbents for medicine", Pharmaceutical magazine, 1995, No. 6, p. 80-85]. Polymethylsiloxane forms a 3D polymeric endless lattice which doesn't have definite molecular mass as shown by the following structure:

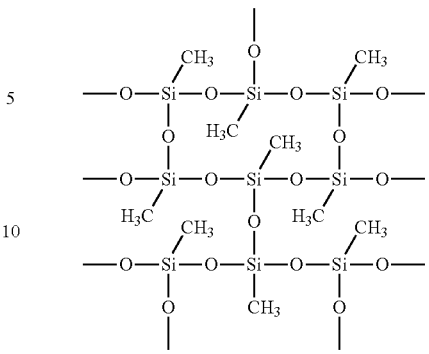

Polymethylsiloxanes are synthesized by means of (1) hydrolysis of methyltrichlorosilane $CH_3SiCl_3$ or methylsilanetriol $CH_3Si(OH)_3$, preferably methyltrichlorosilane, with further (2) exsiccation (drying) of the obtained hydrogel of methylsilicic acid $(CH_3SiO_{1.5}\cdot mH_2O)_\infty$ at a temperature of e.g. 105 to 110° C. till achieving a xerogel with a constant weight:

$$CH_3SiCl_3 + 1.5H_2O + mH_2O \rightarrow (CH_3SiO_{1.5}\cdot mH_2O)_\infty + 3HCl \quad \text{(step 1)}$$

$$(CH_3SiO_{1.5}\cdot mH_2O)_\infty \rightarrow (CH_3SiO_{1.5})_\infty mH_2O \quad \text{(step 2)}.$$

After desiccation the polymethylsiloxane is obtained as a coarsely dispersed product in the form of granules and pieces which are usually milled in a ball mill to a desired particle size. The resulting product—polymethylsiloxane—is a highly dispersed hydrophobic porous powder with the final formula $(CH_3SiO_{1.5})_\infty$. The pore size of the polymethylsiloxane is preferably 5 to 200 nm, more preferably 20 to 100 nm.

Thus, the present invention provides in a ninth aspect a method for preparing polymethylsiloxane comprising the steps (i) hydrolysis of methyltrichlorosilane to obtain a hydrogel of methylsilicic acid;

(ii) drying the obtained hydrogel of methylsilicic acid whereby a coarsely dispersed product in the form of granules and pieces is obtained; and (iii) milling the coarsely dispersed product.

Exemplary methods of preparation of polymethylsiloxane are described in Ukrainian patent UA 82774 C2 and in U.S. patent application US 2010/0240532 A1. The polymethylsiloxane is preferably comprised in the composition of the present invention in an amount of 16.0 to 70.0% by weight, preferably 20 to 45% by weight, based on the total weight of the composition. The particle size of the polymethylsiloxane to be used in the methods of the present invention is preferably 0.01 to 5.0 mm, more preferably 0.1 to 3 mm, even more preferably 0.5 to 2.0 mm.

Polymethylsiloxane provides local wound detoxification due to active sorption of pathogens and low and middle molecular metabolites. Wound exudate fluid is "drained" through a capillary net of the powdered sorbent and organic substances are absorbed into its granules. By raising the pH of the wound it also potentiates the action of a specific antibiotic. Polymethylsiloxane can be used for the applique sorption with or without antibiotics immobilized on its surface. Exemplary preparations are Imosgent and Gentaxan in which the polymethylsiloxane surface is modified by gentamicin.

Polymethylsiloxane is hydrophobic which reduces its healing properties. By mechanochemical immobilization of cationic surfactants onto the polymethylsiloxane, the surface of the resulting surfactant covered polymethylsiloxane particles becomes more hydrophilic.

Cationic surfactants in accordance with the present invention are mono-quaternary or bis-quaternary ammonium compounds or salts of primary and secondary amines. Preferably, the cationic surfactants are mono-quaternary or bis-quaternary ammonium compounds. In accordance with the present invention, a mono-quaternary ammonium compound is a compound having one quaternary ammonium group and a bis-quaternary ammonium compound is a compound having two quaternary ammonium groups. A quaternary ammonium group is a cationic group having 4 organic groups attached to a nitrogen atom. The salts of the quaternary ammonium compounds are preferably chlorides, bromides or iodides. When in the following a specific anion of a cationic surfactant is mentioned, this anion is considered to be a mere example of possible anions to be used with the respective cationic surfactant. Mono-quaternary or bis-quaternary ammonium compounds are known as preparations with high antimicrobial properties.

The cationic surfactant is preferably comprised in the composition of the present invention in an amount of 0.2 to 4.0% by weight, preferably 0.8 to 2.0% by weight, based on the total weight of the composition. The composition of the present invention may comprise a single cationic surfactant or may comprise 2 or more different cationic surfactants.

Exemplary mono-quaternary ammonium compounds are benzalkonium chloride, benzethonium chloride, methylbenzethonium chloride, cetalkonium chloride, cetylpyridinium chloride, cetrimonium, cetrimide, didecyldimethylammonium chloride, myristamidopropyldimethyl-benzammonium chloride (Myramistine®), dofanium chloride, tetraethylammonium bromide, and domiphen bromide. A particularly preferred mono-quaternary ammonium compound is benzalkonium chloride. Benzalkonium chloride is characterized by a wide spectrum of antimicrobial activity. It is used as an antiseptic, antifungal, antiprotozoal, preservative and spermicidal agent [Fleck C. A., "Palliative Dilemmas: Wound Odour", Wound Care Canada, 2006, vol. 4, No 3, p. 10-13].

Preferred bis-quaternary ammonium compounds are ethonium, and decamethoxine. Decamethoxine is most active against gram-positive bacteria, fungi and viruses [Moroz V. M., Paliy G. K., Sobolev V. O. and others. Comparison study of antimicrobal activity of antiseptics; News of Vinnitsa State Medical University, 2002, vol. 2, p. 315-320]. Established is its ability to activate the mononuclear phagocytic system cells. The spectrum of application of ethonium is similar to the spectrum of decametoxine [Gridina T. L., Paliy G. K., Lositskiy V. P., Fedchuk A. S., "Results of the studies of different mechanisms of antiviral activity of decamethoxin and ethonium", Biomedical and Biosocial Anthropology, 2008; vol. 11, p. 43-45]. Octenidine dihydrochloride is a modern antiseptic with a great activity against MRSA [Hubner N. O., Siebert J., Kramer A., "Octenidine dihydrochloride, a modern antiseptic for skin, mucous membranes and wounds", Skin Pharmacol. Physiol., 2010, vol. 23(5), p. 244].

The molecules of the cationic surfactant, which is preferably decamethoxine, interact with the polymethylsiloxane surface by hydrophobic forces without forming covalent bonds and are realized by the attraction between methyl and methylene groups. As result the molecules of cationic surfactant cover the surface of the polymethylsiloxane particles with a continuous layer. This attraction is intensified in an aqueous medium where the cationic surfactant acts as hydrophilizator.

A preferred secondary amine is octenidine dihydrochloride. It is similar in its antimicrobial action to the quaternary ammonium compounds, but is of somewhat broader spectrum of activity.

Besides their antimicrobial effect, cationic surfactants in the composition of the present invention act as detergents that hydrophilize the hydrophobic surface of polymethylsiloxane, facilitating wetting of the hydrophobic surface of polymethylsiloxane. Therefore, a problem of hydrophobic polymethylsiloxane, that the exudate is not absorbed and spreads rapidly under the bandage which promotes skin maceration and activation of the inflammatory process in the wound, has been overcome. Known powder compositions which contain polymethylsiloxane float on the surface of the wound exudate. Furthermore, due to their effect of micellar catalysis, cationic surfactants significantly improve the activity of proteolytic enzymes (synergy effect).

An antimicrobial substance which can be used in the present invention is a compound which is capable of killing microorganisms or inhibiting their growth. For example, the antimicrobial compound may be active against bacteria, viruses, fungi, protozoa, and other microorganisms. The antimicrobial compound may be selective or non-selective for specific classes of microorganisms.

The antimicrobial substance is preferably comprised in the composition of the present invention in an amount of 0.5 to 10.0% by weight, preferably 1.5 to 8.0% by weight, based on the total weight of the composition. The antimicrobial substance used in the present invention may be a single substance or a mixture of two or more substances.

The antimicrobial substance may be selected from one or more compounds belonging to the following classes of compounds which include tetracyclines (e.g. minocycline), rifamycins (e.g. rifampicin), macrolides (e.g. erythromycin), penicillins (e.g. nafcillin), cephalosporins (e.g. cefazolin), other beta-lactam antibiotics (e.g. imipenem, aztreonam, carbacephems, carbapenems), aminoglycosides (e.g. gentamicin), chloramphenicol, sulfonamides (.e. sulfamethoxazole), glycopeptides (e.g. vancomycin), quinolones (e.g. ciprofloxacin), fusidic acid, nitroimidazoles (e.g. metronidazole, tinidazole, nimorazole), thyazoles (e.g. nithazole), mupirocin, polyenes (e.g. amphotericin B), azoles (e.g. fluconazole), beta-lactamase inhibitors (e.g. sulbactam) and oxazolidinones (e.g. linezolid)). Beta-lactam antibiotics are preferably combined with a β-lactamase inhibitor such as clavulanic acid or their salts, sulbactam, or tazobactam. A particularly preferred combination is a composition comprising amoxicillin and potassium clavulanate.

Preferably, the antimicrobial substance used in the present invention does not encompass the above described cationic surfactants, i.e. cationic surfactants are preferably excluded from the meaning of the term "antimicrobial substance".

More preferably, the antimicrobial substances for use in the present invention are metronidazole, ciprofloxacin, fusidic acid, mupirocin, bacitracin, tyrothricin, metal-containing antimicrobials, compounds of boron or other substances with anti-anaerobic or anti-MRSA activity such as penicillin, amoxicillin, oxacillin, gentamycin, linezolid, erythromycin, clindamycin, moxifloxacin, co-trimoxazole, tetracycline, vancomycin, teicoplanin, rifampicin, phosphomycin, tigecycline, daptomycin.

Still more preferred antimicrobial substances for use in the present invention are metronidazole, ciprofloxacin, fusidic acid, mupirocin, bacitracin, tyrothricin, and compounds comprising silver and/or boron.

Preferred antimicrobial substances are metronidazole, ciprofloxacin, fusidic acid, mupirocin, bacitracin, tyrothricin, compounds of silver, compounds of boron or other substances with anti-anaerobic or anti-MRSA activity.

The spectrum of antimicrobial action of metronidazole (1-(β-hydroxyethyl)-3-methyl-5-nitroimidazole) includes simple organisms, anaerobic gram-negative bacteria, bacteroids (including *B. Fragilis*), fusobacteria, anaerobic gram-positive rods (including *Clostridium*), anaerobic gram-positive cocci (*Peptococcus, Peptostreptococcus*). Metronidazole is indicated for anaerobic infections of the skin and soft tissues, bones and joints in the treatment of wounds that do not heal for a long time [Gary R., Woo K. Y., "Local Wound Care for Malignant and Palliative Wounds", Advances in Skin & Wound Care: The Journal for Prevention and Healing, 2010, vol. 23, No 9, p. 417-428].

Ciprofloxacin is a representative of the fluoroquinolones that possesses a high level of activity against a majority of types of microorganisms, both gram-negative and gram-positive. Ciprofloxacin is used in drops and in ointments for local treatment of inflammatory diseases of eye and wounds [Donaldson P. M., Pallett A. P., Carroll M. P., "Ciprofloxacin in general practice", BMJ. (Clinical Research Ed.), May 1994, vol. 308, p. 1437].

Fusidic acid, baktroban (mupirocin), bacitracin, tyrothricin are also antimicrobial substances with high activity against MRSA.

Fusidic acid (chemical formula $C_{31}H_{48}O_6.0.5H_2O$) has antibacterial, bacteriostatic effects and it inhibits bacterial protein synthesis. It is effective against *Staphylococcus* spp., including most strains of *S. aureus* (including MRSA) and *S. epidermidis* (including MRSE) and has activity against *Corynebacterium* spp., *Cladosporium* spp. [Lemaire S., Van Bambeke F., Pierard D., Appelbaum P. C., Tulkens P. M., "Activity of Fusidic Acid Against Extracellular and Intracellular *Staphylococcus aureus*: Influence of pH and Comparison With Linezolid and Clindamycin", CID, 2011, vol. 52 (Suppl. 7), p. S493-503].

Mupirocin (Baktroban®) is an antimicrobial substance which inhibits bacterial protein synthesis. It is an effective bactericidal agent against infections caused by *Staphylococcus aureus*, including MRSA [Sutherland R., Boon R. J., Griffin K. E. et al., "Antibacterial Activity of Mupirocin (Pseudomonic Acid), a New Antibiotic for Topical Use", Antimicrobial Agents and Chemotherapy, 1985, vol. 27(4), p. 495-498].

Bacitracin is an antibiotic produced by strains of the bacteria *B. subtilis*, which is effective against a number of microorganisms. Typically it is used for external application in the treatment of diseases of the skin, eyes or nose, but it can also be administered orally, by injection, or as an intestinal antiseptic. In the food industry it is designated as E700 [European Pharmacopoeia 5.0., 2005, p. 1045-1047].

Tyrothricin is a cyclic polypeptide antibiotic derived from *Bacillus Brevis* that is topically effective against gram-positive bacteria. Tyrothricin contains gramicidin [Tyrosur® Gel-investigation on Wound Healing Efficacy (2010). Clinicaltrials.gov Identifier: NCT01227759. Latest update: Oct. 25, 2010. US National Institute of Health, US National Library of Medicine and US Department of Health & Human Services. Available from: http://clinicaltrials.gov/ct2/show/study/NCT01227759?term=tyrothricin].

Examples of metal-containing antimicrobials are silver, zinc, and copper, and their combined forms including salts, such as chloride, bromide, iodide, nitrate, sulphate, and periodate, complexes with carriers, and other forms.

Compounds comprising silver can be widely used in various medicinal forms for wound treatment, especially for burns. Exemplary compounds of silver are silver nitrate, colloidal silver, and nanosized silver.

Compounds of silver are preferably comprised in the composition of the present invention in an amount of up to 5.0% by weight, preferably 0.01 to 3.0% by weight, based on the total weight of the composition.

Examples of boron-containing antimicrobials for use in the present invention are alkali metal borate, alkaline earth metal borate, amine borate, boric acid and boric esters. Of these boron compounds, metal borates are preferred. These comprise sodium tetraborate, calcium silicate borate, sodium silicate borate, aluminum silicate borate, hydroboracite, aluminum borate, copper borate, magnesium borate, iron borate and zinc borate.

Boron-containing antimicrobials, such as sodium tetraborate, possess specific antibacterial activity against *Pseudomonas aeruginosa*. Another function of sodium tetraborate in some compositions is to turn the pH of the wound contents from acid values (which are caused by inflammation) to normal, i.e. not less than 7.0.

Compounds comprising boron are preferably comprised in the composition of the present invention in an amount of up to 5.0% by weight, preferably 0.01 to 3.0% by weight, based on the total weight of the composition.

In accordance with the present invention, substances with tissue growth activity are substances which can promote cell growth, whereby wound repair can be accelerated. Preferred examples of substances with tissue growth activity are compounds of zinc, methyluracil and growth factors such as epidermal growth factor (EGF), fibroblast growth factor (FGF, e.g. chicken embryo fibroblast-derived growth factor (CDGF)). More preferably, the substances with tissue growth activity are methyluracil and compounds of zinc.

Substances with tissue growth activity are preferably comprised in the composition of the present invention in an amount of up to 10.0% by weight, preferably 0.01 to 5.0% by weight, based on the total weight of the composition.

Compounds comprising zinc are involved in recovery processes in the later stages of wound healing, since zinc is an essential element in the biosynthesis of connective tissue. In addition, these compounds exhibit moderate antimicrobial activity [Bradley M., Cullum N., Nelson E. A. et al., "Systematic reviews of wound care management: (2) Dressings and topical agents used in the healing of chronic wounds", Health Technol. Assess., 1999, vol. 3(17 Pt 2), p. 1-35]. Examples of zinc compounds include zinc oxide, zinc sulfate, and zinc hyaluronate.

Methyluracil is a well known for its tissue growth effect. Methyluracil stimulates the synthesis of nucleic acids and, thus, accelerates the generation of the cells.

Local anesthetics have immunological properties in addition to their direct anesthetic activity. Lidocaine inhibits adhesion, chemotaxis, phagocytosis, and the production of superoxide anion and hydrogen peroxide by neutrophils and macrophages. Local anesthetics may inhibit functions related to natural immunity in neutrophils and macrophages [Azuma Y., Ohura K., "Immunological modulation by lidocaine-epinephrine and prilocaine-felypressin on the functions related to natural immunity in neutrophils and macrophages", Current drug targets. Immune, endocrine and metabolic disorders, 2004, vol. 4(1), p. 29-36]. Lidocaine is included in the ointment «Oflocaine-Darnytsia». Furthermore, lidocaine may be added to the composition of the present invention in the case of pronounced pain. Lidocaine can be comprised in the powder composition of the present invention in an amount of up to 5 wt. %, preferably up to 4 wt. %, more preferably 0.1 to 3 wt. % based on the total weight of the composition of the present invention. When in the present application reference is made to "lidocaine", pharmaceutically acceptable salts of lidocaine are included, in particular lidocaine hydrochloride.

Phenothiazines, herein also referred to as "phenothiazine derivatives", in accordance with the present invention are a class of neuroleptic antipsychotic drugs. A preferred phenothiazine to be used in the present invention is chlorpromazine. Phenothiazines such as chlorpromazine provide the composition of the present invention with unexpected stimulatory effects on the phagocytosis activity of wound macrophages [Cheplyaka O. M., "Complex therapy of patients suffering with anorectal abscess", Dissertation of PhD, Vinnitsa, 2006, p. 21]. Phenothiazines can be comprised in the powder composition of the present invention in an amount of up to 5 wt. %, preferably up to 3 wt. % based on the total weight of the composition of the present invention. Chlorpromazine can preferably be comprised in the powder composition of the present invention in an amount of up to 2 wt. %, more preferably up to 1.5 wt. % based on the total weight of the composition of the present invention.

Proteolytic enzymes in accordance with the present invention are enzymes that conduct proteolysis, i.e., which start protein catabolism by hydrolysis of the peptide bonds that link amino acids together in the polypeptide chain forming the protein. Examples of proteolytic enzymes include trypsin, chemotrypsin, terrylitin, microbial collagenase such as clostridial collagenase, and proteases derived from plants or fungi, such as papain, bromelaine and asperase.

Proteolytic enzymes may be added to the composition in case of treatment of wounds with a great amount of necrotic tissues which need to be decomposed before removal. In surgery enzymes with "soft" necrolytic activity such as trypsin and chemotrypsin and much stronger enzymes of microbial nature such as terrylitin and collagenase are utilized. Proteolytic enzymes can be comprised in the powder composition of the present invention in an amount of up to 3 wt. %, preferably up to 2 wt. % based on the total weight of the composition of the present invention.

Mechanochemical immobilization is a process by which substances such as active ingredients are applied and/or attached (fixed) to the surface of a carrier material.

According to the present invention, the term "mechanochemically immobilized" means that an active ingredient is present on the surface of the particles of a solid carrier material. The carrier material is one of the sorbents used in the present invention, i.e., polymethylsiloxane or highly dispersed silica. E.g., a reference to "a cationic surfactant is mechanochemically immobilized onto polymethylsiloxane" means that the surfactant (active ingredient) is present on the surface of the polymethylsiloxane particles (solid carrier material). Similarly, a reference to "an antimicrobial substance is mechanochemically immobilized onto highly dispersed silica" means that the antimicrobial substance (active ingredient) is present on the surface of the highly dispersed silica particles (solid carrier material). Preferably, the active ingredient forms a molecular layer on the surface of the nanometer sized carrier material particles. Thereby, the total surface of the active ingredient is increased. Thus, the total quantity of active ingredient molecules which are ready to exercise their pharmacological activity in case of "mechanochemical immobilization" is higher than in a composition containing larger particles of the active ingredients.

The mechanochemical immobilization includes two aspects, i.e. (1) a mechanochemical process which is a physical chemical process or chemical reaction initiated by a mechanical process (beating, friction, ultra sonic and so on); and (2) the immobilization. Thus, the mechanochemical immobilization results in physical chemical fixing of the active ingredient on the surface of the carrier material particles with the help of a mechanical process in which impact forces and friction forces are exerted to the components which are mechanochemically immobilized onto each other.

The mechanochemical immobilization is carried out for a certain period of time which is necessary for even immobilization of the active ingredient on the carrier material particles. If the time of the process is too short the result may be a simple mixture of crushed particles of the ingredients.

In step (b2) the mechanochemical immobilization of the antimicrobial substance onto the highly dispersed silica is carried out using only a minor part of the highly dispersed silica since during the mechanochemical immobilization the highly dispersed silica is compressed whereby its sorption properties are reduced. The major part of the highly dispersed silica is not used in step (b2), but is mechanically mixed in step (c) with the mechanochemically immobilized products obtained in step (b).

In step (b2) the weight ratio of the weight of the antimicrobial substance to the weight of the highly dispersed silica is preferably in the range 2:1 to 1:4, more preferably 1.7:1 to 1:3, even more preferably 1.5:1 to 1:2 and most preferably 1.2:1 to 1:1.5. If the weight ratio is in the mentioned range, the surface of highly dispersed silica particles is large enough so that the antimicrobial substance can be fixed on the surface of the particles as a thin even layer of separate molecules which are can easily be released to provide the antimicrobial action.

The process of mechanochemical immobilization can be carried out by any mill as long as it can provide mixing of the material and can exert impact forces and friction forces onto the material to be milled. Alternatively, a mixer, preferably a high-speed mixer with vane, can be employed. The advantage of using a ball mill is a rapid immobilization, while in mixer this process takes more time.

Exemplary mills suitable for carrying out mechanochemical immobilization are tumbling mills such as ball mills or rod mills; agitated ball mills, planetary mills, conus mills, centrifugal mills, VSI mills, jet-streamed mills, jet-mills, pin mills, vibrational mills, and a mixer with vane, i.e. a mixer with blades or paddles. Not suitable for carrying out mechanochemical immobilization is e.g. a hydraulic press because it cannot provide even allocation of the milled substances. Vibrational mills, centrifugal mills, jet-streamed mills and planetary mills are preferred due to their higher productivity. Preferably, the mechanochemical immobilization can be carried out using a ball mill or a vibrational mill. An exemplary ball mill having an internal volume of the drum of 2 liters is produced by the Ukrainian factory "SlavCeramicRefractory", Slavyansk (www.sko.com.ua/melnicisharovye.html).

If a ball mill is used, the speed of rotation should be chosen so that the balls fall and/or tumble inside the mill drum. Thereby the balls can exert impact forces in addition to friction forces on the material which is milled. If the speed of rotation is too low, the balls will simply roll inside the mill and will not exert impact forces. The result may be a roughly blended mixture without even fixation of the active agents on the carrier material. If the speed is too high, the balls will be pressed to the wall of the drum by centrifugal forces so that neither impact forces nor friction forces are exerted.

More preferably, the mechanochemical immobilization can be carried out in ball mill using a porcelain drum having an internal volume of 2 liters at a speed of rotation of 1 rev/sec, i.e. 60 rpm, for a time of 20 to 60 min. For ball mills having a higher drum volume of, e.g., 5, 10, or 50 liters, the time of milling may be higher, e.g., 60 to 120 min. If the duration of the milling is too long, the compression of the carrier material (highly dispersed silica or polymethylsiloxane) is increased which may lead to a partial loss of its sorption qualities.

The composition of the present invention exhibits improved healing properties due to the "mechanochemical immobilization" of the active ingredients on the carrier material.

Figure 2:
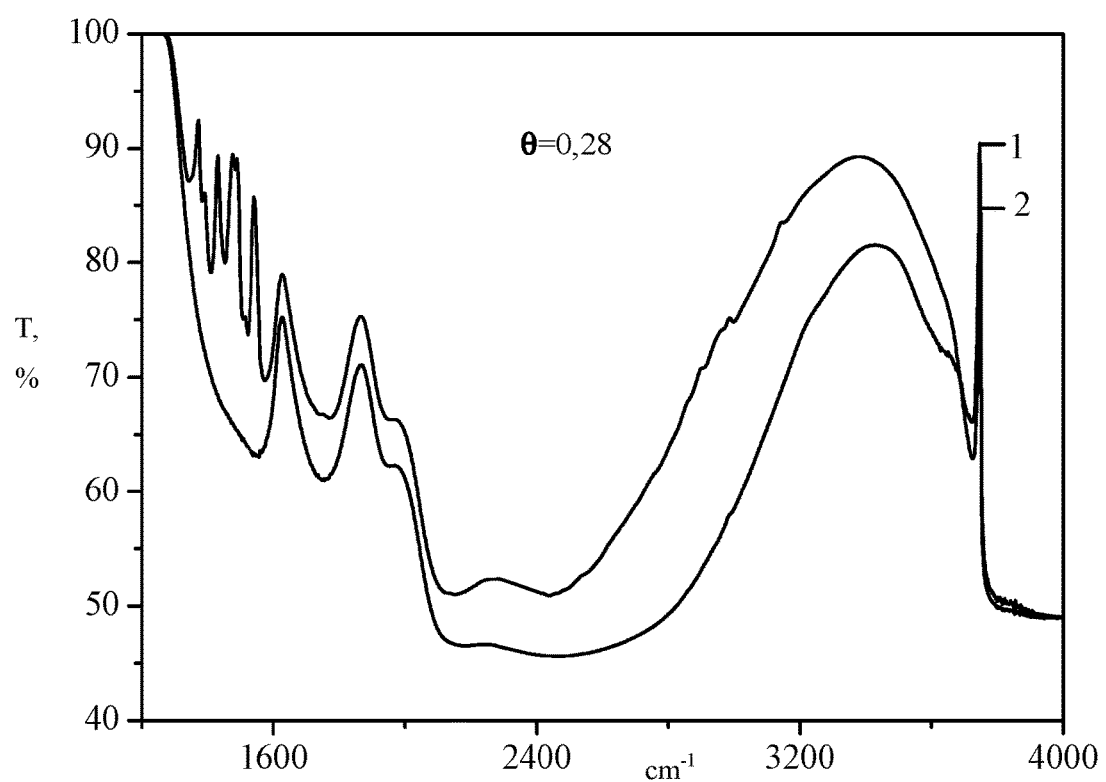
FIG. 2 shows IR-spectra after mechanochemical treatment in a ball mill: the bottom line (line 1) relates to highly dispersed silica treated alone and the upper line (line 2) relates to a treated mixture of highly dispersed silica and metronidazole. This figure shows that 28 wt. % of the metronidazole are immobilized on the highly dispersed silica.

The fact that mechanochemical immobilization took place can be tested by way of X-ray powder diffraction, infrared spectroscopy and other kinds of analysis by means of diagrams before and after the processes as shown in FIGS. 1 and 2.

The composition of the present invention is in the form of a powder. The sorbents polymethylsiloxane and highly dispersed silica with a total content of approximately 90 wt. %, preferably represent 65 to 97 wt. %, more preferably 80 to 95 wt. % of the total weight of the composition, form the powder basis of the composition. The highly dispersed silica particles, polymethylsiloxane particles, and one or both of a cationic surfactant and an antimicrobial substance are the ingredients of the composition which are always present, while other ingredients (i.e., substances with tissue growth activity, lidocaine, phenothiazine derivatives, and proteolytic enzymes) may be added to the basis if needed. Consequently, compositions with a wide range of contents can be prepared depending on the purpose of the treatment. Additionally, depending on the purpose of the treatment different liquid and soft forms may be obtained (suspension, gel, ointment, drops and other) by dispensing the powder composition in a relevant medium. Tablets may be obtained by mixing the composition with excipients and pressing it. Finally, it is possible to include the composition in any aforementioned form in various medicinal articles (dressings, packets, capsules and others) for internal or external use.

The effectiveness of the composition of the present invention for the treatment of wounds is largely due to its sorption properties. Large wounds produce a significant amount of fluid. The removal of exudate from the wound surface is necessary to prevent the reabsorption of toxic breakdown products of necrotic tissues into the body.

Necrolytic properties, along with dehydrative, sorptive and antimicrobial activity make the composition of the present invention a "preparation of choice" for the local treatment of purulent wounds. This applies especially in the case of purulent wounds at anorectal abscesses which are complicated by putrid infection. The use of the composition to accelerate the rejection and breakdown of necrotic tissue allows to avoid necrectomy during repeated surgical interventions and reduces the number of medical manipulations, including dressings.

The high adhesion of the composition to necrotic tissue is particularly important in the treatment of purulent lesion areas in which it is difficult to conduct adequate sanitation by conventional surgical techniques due to the nature of the anatomical location and size of the purulent focus and the duration of the inflammatory process. When retroperitoneal phlegmon is present on a background of pancreatic necrosis using the composition can reduce the duration of drainage by 1.8 times. The use of this composition to accelerate the rejection and lysis of necrotic tissue allows for thorough regular necrectomy in a purulent focus. Thus, due to fragmentation and enhancement of the fluidity of the purulent exudates removal of the lysed tissue via drainages is simplified.

Combined lesion of a limb in a mixed form of the diabetic foot syndrome causes features of a disease, which lead to a weakening of the delimitation mechanisms of the purulent necrotic process, which explains the very high risk of amputation in these patients. The mixed form of diabetic foot syndrome is characterized by protracted infection, even in the case of successful correction of arterial insufficiency. This often manifests itself in a slowdown of the wound repair processes, recurrent necrotic lesions of bone and soft tissue and wound contamination by methicillin-resistant staphylococci. Clearance of purulent inflammation by the composition of the present invention allows to perform reconstructive plastic surgery with preservation of the support function of the foot.

Use of the composition in the surgical treatment of malignant tumors of the larynx, oropharynx and hypopharynx blocks the action of saliva, which shows lytic properties of tissues in the neck and contributes to the spread of the microflora from the oral cavity and pharynx, thereby increasing the duration of healing of postoperative wounds due to the frequent occurrence of wound complications—such as pharyngeal fistulas, skin flap necrosis, wound suppuration and, consequently, neck vessels arrosion—the internal jugular vein and carotid artery, with the emergence of profuse bleeding. The composition effectively cleans the wound from necrotic tissue, even in the case of radiation therapy and chemotherapy. Using the preparation eliminates the need for detoxification and systemic antibiotic therapy, even in cases of multipreparation-resistant wound microflora.

Use of the preparation allows to significantly reduce the quantity of infectious complications of pressure ulcers including bacteremia and sepsis, cellulitis, osteomyelitis, septic arthritis, and sinus tracts or abscesses.

This invention also relates to a method of producing the composition of the present invention which can be realized in two variants (conducted on at least two scales), namely in industrial scale (large scale) corresponding to the third aspect of the present invention which can produce the composition according to the first aspect and pharmacy scale (small scale) corresponding to the fourth aspect of the present invention which can produce the composition according to the second aspect.

The industrial production of the composition includes
(a) providing highly dispersed silica particles, polymethylsiloxane particles, and one or both of a cationic surfactant and an antimicrobial substance, and, optionally, salts of zinc and/or methyluracil and/or lidocaine and/or chlorpromazine, and/or zinc oxide and/or proteolytic enzymes,
(b) carrying out at least one of the following steps (b1) and (b2):
  (b1) mechanochemical immobilization of cationic surfactant onto the polymethylsiloxane,
  (b2) mechanochemical immobilization of antimicrobial substances and, optionally, salts of zinc and/or methyluracil and/or lidocaine and/or chlorpromazine onto a minor part (5 to 30 wt. %, preferably 10 to 20 wt. %, more preferably 11 to 15 wt. % of the total weight of the highly dispersed silica comprised in the composition) of the highly dispersed silica, and
(c) mixing the major part (70 to 95 wt. %, preferably 80 to 90 wt. %, more preferably 85 to 89 wt. %) of the total weight of the highly dispersed silica comprised in the composition of the highly dispersed silica with the products obtained in step (b) and, if necessary, zinc oxide and/or proteolytic enzymes for a time sufficient to obtain finely dispersed, visually homogeneous powder composition. Steps (b1) and (b2) can be carried out sequentially in any order or concomitantly.

Preferably, the industrial production of the composition includes (a) providing highly dispersed silica particles, polymethylsiloxane particles, a cationic surfactant, and an antimicrobial substance, and, optionally, salts of zinc and/or methyluracil and/or lidocaine and/or chlorpromazine, and/or zinc oxide and/or proteolytic enzymes, (b) carrying out the following steps (b1) and (b2):
  (b1) mechanochemical immobilization of cationic surfactant onto the polymethylsiloxane,
  (b2) mechanochemical immobilization of antimicrobial substances and, optionally, salts of zinc and/or methyluracil and/or lidocaine and/or chlorpromazine onto a minor part (5 to 30 wt. %, preferably 10 to 20 wt. %, more preferably 11 to 15 wt. % of the total weight of the highly dispersed silica comprised in the composition) of the highly dispersed silica, and (c) mixing the major part (70 to 95 wt. %, preferably 80 to 90 wt. %, more preferably 85 to 89 wt. %) of the total weight of the highly dispersed silica comprised in the composition of the highly dispersed silica with the products obtained in steps (b1) and (b2) and, if necessary, zinc oxide and/or proteolytic enzymes for a time sufficient to obtain finely dispersed, visually homogeneous powder composition. Steps (b1) and (b2) can be carried out sequentially in any order or concomitantly.

The described pathway includes some novelties that allow to improve the therapeutical efficacy of the product. First of all, mechanochemical immobilization of a cationic surfactant onto the polymethylsiloxane transforms it from hydrophobic to hydrophilic. Thus, the polymethylsiloxane does not separate from the exudate and adheres to the wound surface. Then, due to mechanochemical immobilization of the active agents onto the silica particles they can be better released and, as a result, the activity of the active agents is increased. Both of these properties were not evident and could not have been predicted on the basis of the known properties of cationic surfactants (antimicrobial) and of other active agents (antimicrobial, recovering, anesthetic, etc.).

A more simple way of obtaining of the composition of the present invention ("pharmacy pathway") includes mechanical mixing of polymethylsiloxane, highly dispersed silica, and one or both of a cationic surfactant and an antimicrobial substance, and, further, at least one additional agent selected from the group consisting of substances with tissue growth activity, lidocaine, phenothiazine derivatives, proteolytic enzymes, and combinations thereof at choice for a time sufficient to obtain a finely dispersed, visually homogeneous powder preparation.

According to a preferred embodiment of the present invention the method includes (a) providing highly dispersed silica particles, polymethylsiloxane particles, decamethoxine, and metronidazole, (b1) mechanochemical immobilization of decamethoxine onto the polymethylsiloxane using a ball mill (time of mixing 30-60 minutes, speed of rotation of the drum 0.5-2 rev/sec) or another type of mill; (b2) mechanochemical immobilization of metronidazole onto a minor part of highly dispersed silica using a ball mill (time of mixing 20-60 minutes, speed of rotation of the drum 0.5-2 rev/sec) or another type of mill; and (c) mixing the major part of the highly dispersed silica with the products obtained in steps (b1) and (b2) in a hermetically sealed high-speed mixer with vane, i.e. a mixer with blades or paddles, during a time sufficient to obtain a finely dispersed, visually homogeneous powder composition.

According to a second embodiment of the present invention the method includes (a) providing highly dispersed silica particles, polymethylsiloxane particles, benzalkonium chloride, mupirocin and lidocaine, (b1) mechanochemical immobilization of benzalkonium chloride onto the polymethylsiloxane using a ball mill (time of mixing 30-60 minutes, speed of rotation of the drum 0.5-2 rev/sec) or another type of mill; (b2) mechanochemical immobilization of mupirocin and lidocaine onto a minor part of the highly dispersed silica using a ball mill (time of mixing 30-60 minutes, speed of rotation of the drum 0.5-2 rev/sec) or another type of mill; and (c) mixing the major part of highly dispersed silica with the products obtained in steps (b1) and (b2) in a hermetically sealed high-speed mixer with vane during a time sufficient to obtain a finely dispersed, visually homogeneous powder composition.

In accordance with another embodiment of the present invention, the method includes mixing of polymethylsiloxane, highly dispersed silica, decametoxine, metronidazole and zinc oxide in a hermetically sealed high-speed mixer with vane during a time sufficient to obtain a finely dispersed, visually homogeneous powder. Ethanol or water in an amount of 10 to 60 wt. %, more preferably 25 to 50 wt. % based on sum of the weight of the highly dispersed silica and the polymethylsiloxane (i.e., the sorbents) may be gradually added, during mixing, followed by drying the composition after mixing.

The composition without involving its direct antimicrobial effects leads to a significant reduction of pathogenic properties of microorganisms due to its fast and firm absorption which therefore constitutes an important achievement of the present invention regarding the therapeutic action of the composition in the local treatment of purulent wounds.

Thus, considering the type of the infectious agent, the spectrum of antibacterial activity of the composition of the present invention can be modified in wide range by changing the type and amount of its ingredients.

Taking into consideration the multipurpose property of the proposed compositions to adsorb a large scale of microorganisms and toxins, it can be used for treatment not only of wounds but of a large scope of diseases which have infectional etiology.

Thus, embodiments of the present inventions may be used for treating purulent-inflammatory diseases of soft tissues and visceral organs, as well as human and animals' infections by the following ways of applications:
  application of a pharmaceutical preparation comprising the composition on the wound surface in one of the following forms—powder, gel, ointment, paste, and/or a bandage or absorption package comprising the composition;
  washout and/or irrigation of visceral organs using the suspension form directly or with the help of drainage;
  oral use of a pharmaceutical preparation comprising the composition in liquid form or in the form of a tablet;
  rectal insertion of a pharmaceutical preparation comprising the composition in the form of suppositories and/or with the help of a probe and/or by means of insufflation;
  intraurethral (through urethra) insertion of a suspension of the composition for healing urethritis provoked by gonococci, trichomonases and other infections.

The formulations and ways of application of the composition according to the present invention can be varied in a wide range.

For instance, in addition to the above described ways of usage, the powder may be used in combustiology for the treatment of infected burn surfaces, or in maxillofacial surgery for the treatment of putrid necrotizing phlegmons and noma in maxillofacial region.

The composition in the form of a powder can be used during a larynx or laryngopharynx resection after a cancer surgery when complications arise because saliva gets into the wound.

Powder can be inserted rectally with the help of an insufflator with the aim of treating diseases of the rectum and the large intestine (colonosorption).

A pharmaceutical preparation of the present invention may be used as applique (vulnerosorption), for washing of cavities directly or through a drainpipe, orally (enterosorption), rectal in a kind of suppository, by insufflator or a drainpipe (colonosorption), and by delivery through containers to internal organs, and others.

A pharmaceutical preparation in the form of a suspension of the composition of the present invention in a concentration of 1-4 wt. % may be used for rinsing during an inflammatory disease of the throat, mouth cavity and/or teeth. The composition may be inserted by means of drainage, probe and/or any other means for the treatment of inflammatory diseases of the rectum and the large intestine, organs of abdominal cavity (for example, peritonitis, intra-abdominal and pancreatogenic abscesses, complications after pancreatonecrosis, extraperitoneal phlegmons), inflammatory diseases of the uterus and uterine adnexa, urinary bladder, pleura, bones (osteomyelitis) and other visceral organs. In urological and venereal practice a suspension of the composition is inserted intraurethrally (through the urethra) to heal urethritis caused by gonococci, trichomonases and other infections. A pharmaceutical preparation comprising the composition may be used in the form of drops for the treatment of diseases in the front part of the eyes.

For instance, during surgical treatment of acute intestinal obstruction, adducent and abducent sections of the intestine may be washed out with a 1-4% suspension before getting clear scourage (rinsing waters). Before imposition of anastomosis in the adducent section of intestine, 150-300 ml of a 1-4% suspension of the composition may be inserted and left there.

Another way of usage is postsurgical wash-out by a suspension of the composition via drainage which is set intraoperatively. In traumatic surgery for the treatment of a fistular form of chronic osteomyelitis, a 1-4% suspension of the composition may be inserted into the external foramen of the fistular to achieve full elimination of inflammatory changes.

A suspension of the composition may also be used orally as an enterosorbent during treatment of food intoxication, acute intestinal obstruction and intoxications by any other etiology, for example, a virus. In the case of intoxication, the treatment is started with washing out of the stomach and intestine with a 1-3% suspension of the composition, whereafter it may be applied orally.

Soft forms of the pharmaceutical preparation (gel, ointment, etc.) with concentrations of the composition higher than in a suspension may be used for the local treatment of wounds and impetiginous diseases of the skin. In particular, for the treatment of acne a pharmaceutical preparation may be used as a 15% water gel of the composition. In ointment form the pharmaceutical preparation comprising the composition may be used for the treatment of folliculitis and sycosis in the face and/or diseases provoked by irrational application of cosmetics.

In proctology for the treatment of hemorrhoids, proctitis, anorectal abscess, or anal fissure the pharmaceutical preparation may used by rectal insertion of suppositories comprising the composition of the present invention.

Suppositories comprising the composition can also be inserted intravaginally for sanitation before and after surgery which may include gynecological surgeries, non-specific trichomonal and fungal colpitis, vaginitis, vulvitis, metritis, parametritis, salpingitis.

A pharmaceutical preparation comprising the composition in the form of a tablet and/or of an enterosorbent can be used for the treatment of pharyngitis, or tonsillitis, or as an orally disintegrating tablet for resolution in the mouth cavity in the case of gingivitis and stomatitis.

In the stomatology during local treatment of the parodentium, e.g. against periodontitis, forms of pastes of the pharmaceutical preparation which are prepared ex tempore by mixing the relevant substances such as antiseptic solutions, tincture and herbal extracts with the composition of the invention may be used. The derived pastes may be used for dental application and ultraphoresis.

The composition in the form of a powder and in other forms can be placed inside containers (capsules) for the delivery or prolongation of its shelf life. The composition can be incorporated into drainage bandages, plasters and other bandaging means.

The above mentioned forms of the pharmaceutical preparation may be produced ex tempore (suspension) as well as by factory production (suspension, gel, ointment, drops, tablets, containers, bandages and etc.) by adding the necessary relevant excipients.

For instance, in order to extemporaneously prepare a suspension of the powder composition, the composition may be dispersed in water or I.V. fluid for injection, until it is fully dispersed.

For obtaining an ointment, the powder composition may be dispersed in the ointment base, which is preferably hydrophilic (e.g. a mixture of PEGs with different molecular mass, proxanol, glycerin and others).

The gel form may be obtained by dispersing the powder composition in hydrogels of gelatin, collagen, starch, pectin, polyacrylic acid, polyacrylamide, polyvinylpyrrolidone, polyvinyl alcohol, alginate, derivatives of cellulose and other gel-forming polymers.

In order to obtain a tablet the powder composition may be mixed with microcrystalline cellulose, starch, polyvinylpyrrolidone and/or others additives before conducting granulation.

Suppositories may be obtained by evenly distributing the powder composition in the molten base, which includes cacao butter, alloys of glycerin and gelatin, paraffin and cacao butter or other combinations as additives, and if necessary emulsifiers.

Containers for delivery of the powder composition can be made from porous indissolvable or biodegradable materials (such as gelatin, derivatives from polylactic acid and other materials). For making surgical bandages the powder composition may be pressed into the woven material or filled in penetrable packages with the composition or by using techniques for the relevant process.

The composition of the present invention can be used in the local treatment of purulent and necrotic wounds. In modern surgery one of the most difficult tasks is the local treatment of soft tissues anaerobic infections and nonhealing wounds and ulcers in the conditions of impaired blood supply and innervation. Patients often have problems such as rapid destruction of tissues, slow cleaning of the wound, and generalization of infectious and inflammatory process (SIRS, sepsis). The reasons for these problems can be, e.g., a disorder of microcirculation (diabetic angiopathy, atherosclerosis), or immunosuppression (oncology, chemotherapy, radiation therapy, etc.).

In the 1st phase of wound healing commonly drugs are used that target suppression of infection in the wound, activation of the processes of rejection of necrotic tissues, and evacuation of the wound fluid together with the absorption of products of microbial and tissue decay.

The absorption of wound exudate, tissue and microbial decay products is one of the main goals of the treatment of wounds in the first phase of wound healing. Applicative sorption is a kind of absorption detoxification of the body, which accelerates healing by removing toxins from the wounds.

The advantages of compositions of the present invention which comprise nano-sized sorbents in the treatment of purulent wounds in the 1st phase of wound process are that they well register to the wound surface, that proteins, microorganisms, and toxins are absorbed irreversibly; and that water is absorbed. Thus, the compositions of the present invention provide improved properties compared to ointments which may melt at the body temperature and flow down to the bottom of the wound cavity, which cannot absorb proteins and microorganisms, and which may be diluted by wound exudation.

The use of the composition of the present invention in the complex treatment of anorectal abscess patients, complicated by anaerobic infection and sepsis allows to shorten the duration of the first phase of wound healing due to the rapid wound cleansing from necrotic tissues, diminishing of microbial contamination of the wound, that reduces the duration of hospitalization and indexes of lethality.

In particular, the composition of the present invention can be used in the treatment of acute pelviorectal horseshoe-shaped extrasphincteric abscess, pelviorectal abscess, complicated by putrid infection, wounds after Crile's surgery, bedsore of sacral region, Carbuncle of interscapular region, wounds of calcaneal region, and diabetic foot syndrome.

Furthermore, the composition of the present invention can be used in the treatment of infectious diarrhea, where the sorbents can act as binders of the stool. The action of the composition in the treatment of diarrhea is mainly antibiotic due to the removal of germs and toxins. Thus, the composition can be used in the treatment carbepenem-resistant diarrhea.

The composition of the present invention can also be used in the treatment of infections caused by MRSA, such as pneumonia. A pneumonia can be treated by diluting the composition of the present invention in medical saline solution and inhaling the resulting preparation using a nebulizer.

The composition or the pharmaceutical preparation of the present invention can be used in the treatment of infections caused by *staphylococcus aureus*, methicillin-resistant *staphylococcus aureus* (MRSA), multi-resistant gram-negative bacteria, enterobacteriaceae (e.g., *escherichia coli, klebsiella pneumonia, klebsiella oxytoca, enterobacter cloacae, proteus mirabilis, morganella morganii, serratia marcescens, citrobacter freundii*), and non-fermenting bacteria (e.g., *pseudomonas aeruginosa, acinetobacter baumannii, pseudomonas*).

The term "powder" as used herein and unless defined otherwise, refers to a dry, bulk solid composed of a large number of very fine particles that may flow freely when shaken or tilted. The particle size of the powder is preferably 10 to 2,000 nm, more preferably 50 to 1,000 nm, even more preferably 100 to 500 nm.

In accordance with the present invention, the size of a particle is defined as the volume equivalent diameter of the particle, i.e., the diameter of a spherical particle having the same volume as the particle. The particles size can be measured by photon correlation spectroscopy (PCS). The PCS is a routine method of measuring particle sizes and their particle size distribution (PSD). Usually there are no ideal powders with only one exact size of particles.

Therefore, according to the present invention a specified particle size such as "100 nm" means the number average size of particles which can be derived from the PSD.

It is to be understood that the term "comprising", as used herein and unless defined otherwise, includes the meaning of "consisting essentially of" and the meaning of "consisting of" Accordingly, the term "comprising" may also be understood, in a narrower sense, as "consisting essentially of" or, in an even narrower sense, as "consisting of". The term "consisting essentially of", as used herein and unless defined otherwise, means that the composition can contain further components which do not affect the characteristics of the composition, wherein preferably, the further optional components are contained in an amount of not more than 10% by weight, preferably, not more than 5% by weight, more preferably, not more than 2% by weight, more preferably, not more than 1% by weight with respect to the total weight of the respective composition.

When in the present invention reference is made to a substance as a generic term, such as "cationic surfactant", and it is stated that this generic term "is selected from the group consisting of" a list of specified substances, such as "selected from the group consisting of ethonium, decamethoxine, octenidine dihydrochloride, benzalkonium chloride, myramistine, and combinations thereof", it is to be understood, that the composition of the present invention does not contain any other substances falling under the generic term, except those which are specifically mentioned.

It is to be understood that the term "major part", as used herein and unless defined otherwise, means "more than 50% by weight", preferably "at least 70% by weight". Similarly, the term "minor part", as used herein and unless defined otherwise, means "less than 50% by weight", preferably "not more than 70% by weight".

It is obvious that the present invention is not limited to the above preferred embodiments and various alterations and modifications will become aware to the skilled person.

In particular, the present invention is characterized by the following items:

1. A composition in powder form comprising highly dispersed silica particles, polymethylsiloxane particles, and one or both of a cationic surfactant and an antimicrobial substance, wherein at least one of the following conditions is fulfilled:
    a) at least 25% by weight of the cationic surfactant is present in primary polymethylsiloxane particles carrying the cationic surfactant on their surface and/or in agglomerates of these primary particles; and
    b) at least 25% by weight of the antimicrobial substance is present in primary highly dispersed silica particles carrying the antimicrobial substance on their surface and/or in agglomerates of these primary particles.

2. The composition according to item 1 comprising highly dispersed silica particles, polymethylsiloxane particles, and a cationic surfactant, wherein at least 25% by weight of the cationic surfactant is present in primary polymethylsiloxane particles carrying the cationic surfactant on their surface and/or in agglomerates of these primary particles.

3. The composition according to item 2, wherein the composition further comprises an antimicrobial substance.

4. The composition according to item 1 comprising highly dispersed silica particles, polymethylsiloxane particles and an antimicrobial substance, wherein at least 25% by weight of the antimicrobial substance is present in primary highly dispersed silica particles carrying the antimicrobial substance on their surface and/or in agglomerates of these primary particles.

5. The composition according to item 4, wherein the composition further comprises a cationic surfactant.

6. The composition according to item 1 comprising highly dispersed silica particles, polymethylsiloxane particles, a cationic surfactant and an antimicrobial substance.

7. The composition according to any one of items 1 to 6, wherein at least one of the following conditions is fulfilled:
   a) at least 25% by weight of the cationic surfactant is present in primary polymethylsiloxane particles having the cationic surfactant mechanochemically immobilized onto their surface and/or in agglomerates of these primary particles; and
   b) at least 25% by weight of the antimicrobial substance is present in primary highly dispersed silica particles having the antimicrobial substance mechanochemically immobilized onto the surface of a part of the highly dispersed silica and/or in agglomerates of these primary particles.

8. The composition in powder form according to item 1 comprising highly dispersed silica particles, polymethylsiloxane particles, a cationic surfactant and an antimicrobial substance, wherein
   a) at least 25% by weight of the cationic surfactant is present in primary polymethylsiloxane particles carrying the cationic surfactant on their surface and/or in agglomerates of these primary particles, and
   b) at least 25% by weight of the antimicrobial substance is present in primary highly dispersed silica particles carrying the antimicrobial substance on their surface and/or in agglomerates of these primary particles.

9. The composition according to item 8, wherein
   a) at least 25% by weight of the cationic surfactant is present in primary polymethylsiloxane particles having the cationic surfactant mechanochemically immobilized onto their surface and/or in agglomerates of these primary particles, and
   b) at least 25% by weight of the antimicrobial substance is present in primary highly dispersed silica particles having the antimicrobial substance mechanochemically immobilized onto the surface of a part of the highly dispersed silica and/or in agglomerates of these primary particles.

10. The composition according to item 7 or 9, wherein the part of the highly dispersed silica onto which the antimicrobial substance is mechanochemically immobilized is 5 to 30 wt. %, preferably 10 to 20 wt. %, more preferably 11 to 15 wt. % of the total weight of the highly dispersed silica comprised in the composition.

11. The composition according to any one of items 1 to 7, wherein the composition comprises
    21.0 to 75.0 wt. % of the highly dispersed silica;
    16.0 to 70.0 wt. % of the polymethylsiloxane; and
    at least one of a cationic surfactant in an amount of 0.2 to 4.0 wt. %, and an antimicrobial substance in an amount of 0.5 to 10 wt. %;
    based on the total weight of the composition.

12. The composition according to item 11, wherein the composition comprises
    35.0 to 70.0 wt. % of the highly dispersed silica;
    20.0 to 45.0 wt. % of the polymethylsiloxane;
    at least one of a cationic surfactant in an amount of 0.8 to 2.0 wt. %, and an antimicrobial substance in an amount of 1.5 to 8 wt. %;
    based on the total weight of the composition.

13. The composition according to any one of items 1 to 11, wherein the composition comprises
    21.0 to 75.0 wt. % of the highly dispersed silica,
    16.0 to 70.0 wt. % of the polymethylsiloxane,
    0.2 to 4.0 wt. % of the cationic surfactant, and
    0.5 to 10 wt. % of the antimicrobial substance,
    based on the total weight of the composition.

14. The composition according to item 13, wherein the composition comprises
    35.0 to 70.0 wt. % of the highly dispersed silica,
    20.0 to 45.0 wt. % of the polymethylsiloxane,
    0.8 to 2.0 wt. % of the cationic surfactant, and
    1.5 to 8 wt. % of the antimicrobial substance,
    based on the total weight of the composition.

15. The composition according to any one of items 1 to 14, further comprising at least one additional agent selected from the group consisting of substances with tissue growth activity, lidocaine, phenothiazine derivatives, proteolytic enzymes, and combinations thereof.

16. The composition according to item 15, wherein the composition comprises at least one of the following agents:
    0.01 to 10.0 wt. % of at least one substance with tissue growth activity,
    0.01 to 5.0 wt. % lidocaine,
    0.01 to 5.0 wt. % of at least one phenothiazine derivative, and
    0.01 to 3.0 wt. % of at least one proteolytic enzyme,
    based on the total weight of the composition.

17. A composition in powder form comprising:
    21.0 to 75.0 wt. % of highly dispersed silica;
    16.0 to 70.0 wt. % of polymethylsiloxane;
    at least one of a cationic surfactant in an amount of 0.2 to 4.0 wt. % and an antimicrobial substance in an amount of 0.5 to 10 wt. %;
    and further at least one of the following agents:
    0.01 to 10.0 wt. % of at least one substance with tissue growth activity,
    0.01 to 5.0 wt. % lidocaine,
    0.01 to 5.0 wt. % of at least one phenothiazine derivative, and
    0.01 to 3.0 wt. % of at least one proteolytic enzyme,
    based on the total weight of the composition.

18. The composition according to item 17 comprising:
    21.0 to 75.0 wt. % of highly dispersed silica;
    16.0 to 70.0 wt. % of polymethylsiloxane;
    0.2 to 4.0 wt. % of a cationic surfactant;
    0.5 to 10 wt. % of an antimicrobial substance;
    and at least one of the following agents:
    0.01 to 10.0 wt. % of at least one substance with tissue growth activity,
    0.01 to 5.0 wt. % lidocaine, 0.01 to 5.0 wt. % of at least one phenothiazine derivative, and 0.01 to 3.0 wt. % of at least one proteolytic enzyme, based on the total weight of the composition.

19. The composition according to any one of items 1 to 18, wherein the sum of the highly dispersed silica and the polymethylsiloxane represents 65 to 97 wt. %, preferably 80 to 95 wt. % of the total weight of the composition.

20. The composition according to any one of items 1 to 19, wherein the highly dispersed silica is selected from the group consisting of fumed silica, precipitated silica, colloidal anhydrous silica, silicagel, Syloid, Aerosil, and combinations thereof 21. The composition according to any one of items 1 to 20, wherein the cationic surfactant is selected from mono- or bis-quaternary ammonium compounds.

22. The composition according to any one of items 1 to 21, wherein the cationic surfactant is selected from the group consisting of ethonium, decamethoxine, octenidine dihydrochloride, benzalkonium chloride, myramistine, and combinations thereof 23. The composition according to any one of items 1 to 22, wherein the antimicrobial substance is selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof 24. A method of producing a composition in powder form comprising the following steps (a) to (c):
    (a) providing highly dispersed silica particles, polymethylsiloxane particles, and one or both of a cationic surfactant and an antimicrobial substance;
    (b) carrying out at least one of the following steps (b1) and (b2):
        (b1) forming primary polymethylsiloxane particles carrying the cationic surfactant on their surface and/or agglomerates of these primary particles, and
        (b2) forming primary highly dispersed silica particles carrying the antimicrobial substance on their surface and/or agglomerates of these primary particles using a minor part of the highly dispersed silica particles; and
    (c) mixing the major part of the highly dispersed silica particles with the products obtained in step (b).

25. The method according to item 24, wherein the cationic surfactant is provided in step (a), primary polymethylsiloxane particles carrying the cationic surfactant on their surface and/or in agglomerates of these primary particles are formed in step (b2), and all of the highly dispersed silica particles are employed in step (c).

26. The method according to item 24, wherein the antimicrobial substance is provided in step (a), and primary highly dispersed silica particles carrying the antimicrobial substance on their surface and/or in agglomerates of these primary particles using a minor part of the highly dispersed silica particles are formed in step (b1).

27. The method according to item 24, wherein the cationic surfactant and the antimicrobial substance are provided in step (a).

28. The method according to item 27, wherein step (b1) is carried out, in a step (b2') a minor part of the highly dispersed silica particles is mixed with the antimicrobial substance, and in step (c) the major part of the highly dispersed silica particles is mixed with the products obtained in steps (b1) and (b2').

29. The method according to item 27, wherein step (b1) is carried out, and in step (c) all of the highly dispersed silica particles are mixed with the product obtained in step (b1) and the antimicrobial substance.

30. The method according to item 27, wherein step (b2) is carried out, in a step (b1') the polymethylsiloxane particles are mixed with the cationic surfactant, and in step (c) the major part of the highly dispersed silica particles is mixed with the products obtained in steps (b1') and (b2).

31. The method according to item 27, wherein step (b2) is carried out, and in step (c) the major part of the highly dispersed silica particles is mixed with the product obtained in steps (b2), the polymethylsiloxane particles and the cationic surfactant.

32. the method of producing a composition in powder form according to item 24 comprising the following steps (a) to (c):
    (a) providing highly dispersed silica particles, polymethylsiloxane particles, a cationic surfactant, and an antimicrobial substance;
    (b) carrying out the following steps (b1) and (b2):
        (b1) forming primary polymethylsiloxane particles carrying the cationic surfactant on their surface and/or agglomerates of these primary particles, and
        (b2) forming primary highly dispersed silica particles carrying the antimicrobial substance on their surface and/or agglomerates of these primary particles using a minor part of the highly dispersed silica particles; and
    (c) mixing the major part of the highly dispersed silica particles with the products obtained in step (b).

33. The method according to any one of items 27 to 32, wherein the major part of the highly dispersed silica particles employed in step (c) represents 70 to 95 wt. %, preferably 80 to 90 wt. %, more preferably 85 to 89 wt. % of the total weight of the highly dispersed silica comprised in the composition and the remaining highly dispersed silica particles form the minor part of the highly dispersed silica particles employed in step (b2).

34. The method according to any one of items 24 to 26, wherein the composition comprises
    21.0 to 75.0 wt. % of the highly dispersed silica,
    16.0 to 70.0 wt. % of the polymethylsiloxane, and
    at least one of a cationic surfactant in an amount of 0.2 to 4.0 wt. %, and an antimicrobial substance in an amount of 0.5 to 10 wt. %, based on the total weight of the composition.

35. The method according to item 34, wherein the composition comprises
    35.0 to 70.0 wt. % of the highly dispersed silica,
    20.0 to 45.0 wt. % of the polymethylsiloxane, and
    at least one of a cationic surfactant in an amount of 0.8 to 2.0 wt. %, and an antimicrobial substance in an amount of 1.5 to 8 wt. %,
    based on the total weight of the composition.

36. The method according to any one of items 27 to 33, wherein the composition comprises
    21.0 to 75.0 wt. % of the highly dispersed silica,
    16.0 to 70.0 wt. % of the polymethylsiloxane,
    0.2 to 4.0 wt. % of the cationic surfactant, and
    0.5 to 10 wt. % of the antimicrobial substance,
    based on the total weight of the composition.

37. The method according to item 36, wherein the composition comprises 35.0 to 70.0 wt. % of the highly dispersed silica,
20.0 to 45.0 wt. % of the polymethylsiloxane,
0.8 to 2.0 wt. % of the cationic surfactant, and
1.5 to 8 wt. % of the antimicrobial substance,
based on the total weight of the composition.

38. The method according to any one of items 24 to 37, wherein the composition further comprises at least one additional agent selected from the group consisting of substances with tissue growth activity, lidocaine, phenothiazine derivatives, proteolytic enzymes, and combinations thereof 39. The method according to item 38, wherein the composition comprises at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme, based on the total weight of the composition.

40. The method according to item 38 or 39, wherein the primary particles of the highly dispersed silica formed in step (b2) carry the antimicrobial substance and at least one further substance selected from the group consisting of compounds having tissue growth activity, lidocaine, and phenothiazine derivatives on their surface.

41. The method according to item 40, wherein the primary particles of the highly dispersed silica formed in step (b2) carry the antimicrobial substance and at least one further substance selected from the group consisting of salts of zinc, methyluracil, lidocaine, and chlorpromazine on their surface.

42. The method according to any one of items 38 to 41, wherein in step (c) the major part of the highly dispersed silica is mixed with the products obtained from steps (b1) and (b2) and at least one component selected from zinc oxide, and proteolytic enzymes.

43. The method according to any one of items 24 to 42, wherein the formation of the primary particles or their agglomerates in steps (b1) and (b2) is achieved by milling the respective components.

44. The method according to item 43, wherein the milling is carried out using a ball mill or a vibrational mill.

45. The method according to item 44, wherein the milling in step (b1) is carried out using a ball mill, the time of milling is 30-60 minutes, and the speed of rotation of the drum is 0.5-2 rev/sec.

46. The method of item 44 or 45, wherein the milling in step (b2) is carried out using a ball mill, the time of milling is 20-60 minutes, and the speed of rotation of the drum is 0.5-2 rev/sec.

47. The method according to any one of items 24 to 46, wherein step (c) is carried out using a hermetically sealed high-speed mixer with vane.

48. The method according to any one of items 24 to 47, wherein
in step (b1) the cationic surfactant is mechanochemically immobilized onto the polymethylsiloxane particles; and
in step (b2) the antimicrobial substance and optionally at least one further substance selected from the group consisting of compounds having tissue growth activity, lidocaine, and phenothiazine derivatives are mechanochemically immobilized onto the highly dispersed silica particles.

49. A method of producing a composition in powder form comprising mechanical mixing of:

21.0 to 75.0 wt. % of the highly dispersed silica;
16.0 to 70.0 wt. % of the polymethylsiloxane;
at least one of a cationic surfactant in an amount of 0.2 to 4.0 wt. % and an antimicrobial substance in an amount of 0.5 to 10 wt. %;
and further at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme, based on the total weight of the composition.

50. The method of producing a composition in powder form according to item 49 comprising mechanical mixing of:
21.0 to 75.0 wt. % of the highly dispersed silica;
16.0 to 70.0 wt. % of the polymethylsiloxane;
0.2 to 4.0 wt. % of the cationic surfactant;
0.5 to 10 wt. % of the antimicrobial substance;
and at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme, based on the total weight of the composition.

51. The method according item 49 or 50, wherein the mixing is carried out using a hermetically sealed high-speed mixer with vane.

52. The method according any one of items 49 to 51, wherein ethanol or water in an amount of 25 to 50 wt. % based on sum of the weight of the highly dispersed silica and the polymethylsiloxane is gradually added during mixing, and the composition is dried after mixing.

53. The method according to any one of items 24 to 52, wherein the sum of the highly dispersed silica and the polymethylsiloxane represents 65 to 97 wt. %, preferably 80 to 95 wt. % of the total weight of the composition.

54. The method according to any one of items 24 to 53, wherein the highly dispersed silica is selected from the group consisting of fumed silica, precipitated silica, colloidal anhydrous silica, silicagel, Syloid, Aerosil, and combinations thereof 55. The method according to any one of items 24 to 54, wherein the cationic surfactant is selected from mono- or bis-quaternary ammonium compounds.

56. The method according to item 55, wherein the cationic surfactant is selected from the group consisting of ethonium, decamethoxine, octenidine dihydrochloride, benzalkonium chloride, myramistine, and combinations thereof 57. The method according to any one of items 24 to 56, wherein the antimicrobial substance is selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof 58. A composition in powder form obtainable by the method according to any one of items 24 to 57.

59. Pharmaceutical preparation which is or comprises the composition according to any one of items 1 to 23 or 58.

60. The pharmaceutical preparation according to item 59 which is the composition according to any one of items 1 to 23 or 58

61. The pharmaceutical preparation according to item 59 or 60 in form of a powder, a suspension, a gel, an ointment, drops, a suppository, or a tablet.
62. Medical article selected from the group consisting of a dressing, packets, or capsules, comprising the pharmaceutical preparation according to any one of items 59 to 61.
63. The composition according to any one of items 1 to 23 or 58 or the pharmaceutical preparation according to any one of items 59 to 61 for use in the treatment of purulent wounds and necrotic wounds.
64. The composition according to any one of items 1 to 23 or 58 or the pharmaceutical preparation according to any one of items 59 to 61 for use in the treatment of infected burn surfaces, putrid necrotizing phlegmons and noma in the maxillofacial region, wounds during a larynx or laryngopharynx resection after a cancer surgery, inflammatory diseases of the throat, mouth cavity and/or teeth, pharyngitis, tonsillitis, gingivitis and stomatitis, periodontitis, dental application and ultraphoresis, diseases of the rectum, the large intestine and organs of abdominal cavity, peritonitis, intra-abdominal and pancreatogenic abscesses, complications after pancreatonecrosis, extraperitoneal phlegmons, inflammatory diseases of the uterus and uterine adnexa, urinary bladder, pleura, bones, and other visceral organs, osteomyelitis, urethritis caused by gonococci, trichomonases and other infections, diseases in the front part of the eyes, a fistular in traumatic surgery, food intoxication, acute intestinal obstruction and intoxications by a virus, wounds and impetiginous diseases of the skin, acne, folliculitis and sycosis in the face and/or diseases provoked by irrational application of cosmetics, hemorrhoids, proctitis, anorectal abscesses, anal fissures, wounds after gynecological surgeries, non-specific trichomonal and fungal colpitis, vaginitis, vulvitis, metritis, parametritis, salpingitis, infectious diarrhea, infections caused by *staphylococcus aureus*, methicillin-resistant *staphylococcus aureus* (MRSA), multi-resistant gram-negative bacteria, enterobacteriaceae, and non-fermenting bacteria.
65. Composition in powder form comprising polymethylsiloxane particles and a cationic surfactant, wherein at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles.
66. The composition according to item 65, wherein at least 50% by weight of the cationic surfactant is present in primary polymethylsiloxane particles carrying the cationic surfactant on their surface or in agglomerates of these primary particles.
67. The composition in powder form according to item 65 or 66 comprising polymethylsiloxane particles and a cationic surfactant, wherein at least 25% by weight, preferably 25 to 80% by weight, more preferably 40 to 80% by weight, most preferably 40 to 60% by weight of the cationic surfactant is present in primary polymethylsiloxane particles having the cationic surfactant mechanochemically immobilized onto their surface and/or in agglomerates of these primary particles.
68. The composition according to item 67, wherein at least 50% by weight of the cationic surfactant is mechanochemically immobilized onto the polymethylsiloxane.
69. The composition according to any one of items 65 to 68, wherein the composition comprises:
90.0 to 99.8 wt. % of the polymethylsiloxane, and
0.2 to 10 wt. % of the cationic surfactant,
based on the total weight of the composition.
70. The composition according to item 69, wherein the composition comprises:
95.0 to 99.0 wt. % of the polymethylsiloxane, and
1 to 5.0 wt. % of the cationic surfactant,
based on the total weight of the composition.
71. The composition according to any one of items 65 to 70, wherein the composition does not contain highly dispersed silica and/or an antimicrobial substance different from the cationic surfactant.
72. The composition according to any one of items 65 to 70, wherein the composition consists of polymethylsiloxane particles and a cationic surfactant.
73. The composition according to any one of items 65 to 72, wherein the cationic surfactant is selected from mono- or bis-quaternary ammonium compounds. More preferably, the cationic surfactant is selected from the group consisting of ethonium, decamethoxine, octenidine dihydrochloride, benzalkonium chloride, myramistine, and combinations thereof
74. Composition in powder form comprising highly dispersed silica particles and an antimicrobial substance, wherein at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles.
75. The composition according to item 74, wherein at least 50% by weight of the antimicrobial substance is present in primary highly dispersed silica particles carrying the antimicrobial substance on their surface or in agglomerates of these primary particles.
76. The composition in powder form according to item 74 or 75 comprising highly dispersed silica particles and an antimicrobial substance, wherein at least 25% by weight, preferably 25 to 80% by weight, more preferably 40 to 80% by weight, most preferably 40 to 60% by weight of the antimicrobial substance is present in primary highly dispersed silica particles having the antimicrobial substance mechanochemically immobilized onto the surface of a part of the highly dispersed silica and/or in agglomerates of these primary particles.
77. The composition according to item 76, wherein the part of the highly dispersed silica onto which the antimicrobial substance is mechanochemically immobilized is 5 to 30 wt. %, preferably 10 to 20 wt. %, more preferably 11 to 15 wt. % of the total weight of the highly dispersed silica comprised in the composition.
78. The composition according to item 77, wherein at least 50% by weight of the antimicrobial substance is mechanochemically immobilized onto a part of the highly dispersed silica representing 10 to 20 wt. % of the total weight of the highly dispersed silica comprised in the composition.
79. The composition according to any one of items 74 to 78, wherein the composition comprises:
80.0 to 99.5 wt. % of the highly dispersed silica, and
0.5 to 20 wt. % of the antimicrobial substance,
based on the total weight of the composition.
80. The composition according to item 79, wherein the composition comprises:
85 to 98.5 wt. % of the highly dispersed silica, and
1.5 to 15 wt. % of the antimicrobial substance,
based on the total weight of the composition.

81. The composition according to any one of items 74 to 80, wherein the composition does not contain polymethylsiloxane and/or a cationic surfactant.
82. The composition according to any one of items 74 to 80 wherein the composition consists of highly dispersed silica particles and an antimicrobial substance.
83. The composition according to any one of items 74 to 82, wherein the highly dispersed silica is selected from the group consisting of fumed silica, precipitated silica, colloidal anhydrous silica, silicagel, Syloid®, Aerosil®, and combinations thereof
84. The composition according to any one of items 74 to 83, wherein the antimicrobial substance is selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof
85. A method of producing a composition in powder form comprising the following steps:
    (a) providing polymethylsiloxane particles and a cationic surfactant;
    (b1) forming primary polymethylsiloxane particles carrying the cationic surfactant on their surface and/or in agglomerates of these primary particles.
86. The method according to item 85, wherein at least 25% by weight, preferably 25 to 80% by weight, more preferably 40 to 80% by weight, most preferably 40 to 60% by weight of the cationic surfactant is present in primary polymethylsiloxane particles carrying the cationic surfactant on their surface or in agglomerates of these primary particles.
87. The method according to item 86, wherein at least 50% by weight of the cationic surfactant is present in primary polymethylsiloxane particles carrying the cationic surfactant on their surface or in agglomerates of these primary particles.
88. The method according to any one of items 85 to 87, wherein the composition comprises:
    90.0 to 99.8 wt. % of the polymethylsiloxane, and
    0.2 to 10 wt. % of the cationic surfactant,
    based on the total weight of the composition.
89. The method according to item 88, wherein the composition comprises:
    95.0 to 99.0 wt. % of the polymethylsiloxane, and
    1 to 5.0 wt. % of the cationic surfactant,
    based on the total weight of the composition.
90. The method according to any one of items 85 to 89, wherein the cationic surfactant is mechanochemically immobilized onto the polymethylsiloxane particles in step (b1).
91. A composition in powder form obtainable by the method according to any one of items 85 to 90.
92. A method of producing a composition in powder form comprising the following steps:
    (a) providing highly dispersed silica particles and an antimicrobial substance;
    (b2) forming primary highly dispersed silica particles carrying the antimicrobial substance on their surface and/or in agglomerates of these primary particles using a minor part of the highly dispersed silica particles; and
    (c) mixing the major part of the highly dispersed silica particles with the products obtained in step (b2).
93. The method according to item 92, wherein at least 25% by weight, preferably 25 to 80% by weight, more preferably 40 to 80% by weight, most preferably 40 to 60% by weight of the antimicrobial substance is present in primary highly dispersed silica particles carrying the antimicrobial substance on their surface or in agglomerates of these primary particles.
94. The method according to item 93, wherein at least 50% by weight of the antimicrobial substance is present in primary highly dispersed silica particles carrying the antimicrobial substance on their surface or in agglomerates of these primary particles.
95. The method according to any one of items 92 to 94, wherein the major part of the highly dispersed silica particles employed in step (c) represents 70 to 95 wt. %, preferably 80 to
    90 wt. %, more preferably 85 to 89 wt. % of the total weight of the highly dispersed silica comprised in the composition.
96. The method according to any one of items 92 to 95, wherein the composition comprises:
    80.0 to 99.5 wt. % of the highly dispersed silica, and
    0.5 to 20 wt. % of the antimicrobial substance,
    based on the total weight of the composition.
97. The method according to item 96, wherein the composition comprises:
    85 to 98.5 wt. % of the highly dispersed silica, and
    1.5 to 15 wt. % of the antimicrobial substance,
    based on the total weight of the composition.
98. The method according to any one of items 92 to 97, wherein the primary particles of the highly dispersed silica formed in step (b2) carry the antimicrobial substance and at least one further substance selected from the group consisting of compounds having tissue growth activity, lidocaine, and phenothiazine derivatives on their surface.
99. The method according to item 98, wherein the primary particles of the highly dispersed silica carry the antimicrobial substance and at least one further substance selected from the group consisting of salts of zinc, methyluracil, lidocaine, and chlorpromazine on their surface.
100. The method according to any one of items 92 to 99, wherein in step (c) the major part of the highly dispersed silica is mixed with the products obtained from step (b2) and at least one component selected from zinc oxide, and proteolytic enzymes.
101. The method according to any one of items 92 to 100, wherein the antimicrobial substance and optionally at least one further substance selected from the group consisting of compounds having tissue growth activity, lidocaine, and phenothiazine derivatives are mechanochemically immobilized onto the highly dispersed silica particles in step (b2).
102. The method according to any one of items 92 to 101, wherein the minor part of the highly dispersed silica particles employed in step (b2) represents 5 to 30 wt. %, preferably 10 to 20 wt. %, more preferably 11 to 15 wt. % of the total weight of the highly dispersed silica comprised in the composition.
103. The method according to item 102, wherein the remaining highly dispersed silica particles form the major part of the highly dispersed silica particles employed in step (c), which preferably represents 70 to 95 wt. %, more preferably 80 to 90 wt. %, most preferably 85 to 89 wt. % of the total weight of the highly dispersed silica comprised in the composition.
103. A composition in powder form obtainable by the method according to any one of items 92 to 102.
104. A kit comprising separately the composition according to any one of items 65 to 73 or 91 and highly dispersed silica particles.

105. A kit comprising separately the composition according to any one of items 74 to 82 or 103 and polymethylsiloxane particles.

106. A kit comprising separately the composition according any one of items 65 to 73 or 91 and the composition according to any one of items 74 to 82 or 103.

107. A method for preparing polymethylsiloxane comprising the steps
   (i) hydrolysis of methyltrichlorosilane to obtain a hydrogel of methylsilicic acid;
   (ii) drying the obtained hydrogel of methylsilicic acid whereby a coarsely dispersed product in the form of granules and pieces is obtained; and
   (iii) milling the coarsely dispersed product.

108 The method according to item 107, wherein the drying step (ii) is carried out at a temperature of about 105 to about 110° C. till achieving a xerogel with a constant weight.

109. The method according to item 107 or 108, wherein the milling in step (iii) is carried out using a ball mill.

110. The method according to any one of items 107 to 109, wherein the specific surface area of the resulting polymethylsiloxane is 100 to 1,000 $m^2/g$, preferably 300 to 700 $m^2/g$, more preferably 400 to 600 $m^2/g$.

111. The method according to any one of items 107 to 110, wherein the pore size of the resulting polymethylsiloxane is 5 to 200 nm, preferably 20 to 100 nm.

112. Polymethylsiloxane obtainable by the method according to any one of items 107 to 111.

113. The composition according to any one of items 1 to 23 or 58, wherein the polymethylsiloxane comprised in the composition is a polymethylsiloxane according to item 112.

114. The method according to any one of items 24 to 57, wherein the polymethylsiloxane employed in the method is a polymethylsiloxane according to item 115.

EXAMPLES

In the examples the following substances have been employed:

Highly dispersed silica having a specific surface area of 300 $m^2$ per 1 gram (pilot production of the Institute of Surface Chemistry of the National Academy of Sciences of Ukraine, Kalush city);

Methylsilicic acid hydrogel form JSC Kreoma-pharm, Kiev, polymethylsiloxane was obtained from this gel by means of exsiccation (drying):

Metronidazole of pharmacological purity (China);

Decamethoxine (pilot production of the Institute of Organic Chemistry of the National Academy of Science of Ukraine, Kiev);

Zinc oxide of pharmacological purity (Holland);

semipermeable membrane—film from food cellophane;

gelatin (distributor of chemical reagents "Aldrich" or any other food gelatin);

mixture of amino acids—medicinal substance "Aminosteril" (Fresenius-Kabi Austria GmbH);

Agar-agar (Mahachkalinsky plant of substrates, Russia).

The process of mechanical chemical immobilization was made in a ball mill (SlavCeramic Ltd, Slavyansk, Ukraine) having a porcelain drum of 2 liters volume with porcelain cylinders as milling elements which filled 50% of the drum volume.

The method of obtaining of the composition of the present invention is further illustrated by the following non-limiting Examples 1-3. In Examples 1 and 2 the composition is produced by a method comprising three steps: (b), (c) and (d). Step (a) which relates to the provision of the components is not explicitly mentioned. In steps (b) and (c) an excessive amount of intermediate products ("in reserve") is prepared, in step (d) a total of 100 g of finished product is obtained. In Example 3 which represents the pharmacy variant (fourth aspect of the invention) the composition is produced in by only one step. All operations are performed under aseptic conditions.

Example 1

(Production of a composition for wound healing in the first, exudative phase of the wound healing process, with a predominance of anaerobic microorganisms): (b) 140.0 g of polymethylsiloxane and 7.5 g of decamethoxine were placed in the porcelain drum of a ball mill and mixed at a speed of 1 rev/sec for 60 min, (c) 50.0 g of highly dispersed silica and 50.0 g of metronidazole were placed in the porcelain drum of a ball mill and mixed at a speed of rotation of 1 rev/sec for 45 min; (d) 55.5 g of highly dispersed silica, 29.5 g of product (b) and 15.0 g of product (c) were placed in a sealed high-speed mixer with vane and stirred for 10 minutes. The resulting composition was packed, and marked.

Example 2

(Production of a composition for wound healing in the first phase of the wound healing process with pronounced pain syndrome and prevalence of gram-positive microorganisms): (b) 150.0 g of polymethylsiloxane and 5.0 g of benzalkonium chloride were placed in a vibrational mill and processed for 15 min at 1500-3000 oscillations per minute and an amplitude of 2-4 millimeters; (c) 45.0 g of highly dispersed silica, 12.0 g of mupirocin and 12.0 g of lidocaine hydrochloride were placed in a vibrational mill and processed for 10 min at 1500-3000 oscillations per minute and an amplitude of 2-4 millimeters; (d) 57.5 g of highly dispersed silica, 31.0 g of product (b) and 11.5 g of product (c) were placed in a sealed high-speed mixer with vane and stirred for 10 minutes. The resulting composition was packed, and marked.

Example 3

(Production of a composition for wound healing in the second reparative phase of the wound healing process): 43.0 g of polymethylsiloxane, 41.0 g of highly dispersed silica, 1.5 g of decamethoxine, 4.5 g of metronidazole and 10.0 g of zinc oxide were placed in a hermetically sealed high-speed mixer with vane and mixed for 4 hours. 30 g of ethanol were added gradually during mixing. The resulting composition was dried, packed, and marked.

The amounts of the ingredients of the compositions produced in Examples 1-3 are given in Table 1.

TABLE 1

Amounts (in wt %) of the ingredients of the compositions produced in Examples 1-3

| Name of ingredients | Examples | | |
| --- | --- | --- | --- |
| | 1 | 2 | 3 |
| Highly dispersed silica | 63.0 | 65.0 | 41.0 |
| Polymethylsiloxane | 28.0 | 30.0 | 43.0 |
| Decamethoxine | 1.5 | — | 1.5 |

TABLE 1-continued

Amounts (in wt %) of the ingredients of
the compositions produced in Examples 1-3

| Name of ingredients | Examples | | |
|---|---|---|---|
| | 1 | 2 | 3 |
| Benzalkonium chloride | — | 1.0 | — |
| Metronidazole | 7.5 | — | 4.5 |
| Mupirocin | — | 2.0 | — |
| Zinc oxide | — | — | 10.0 |
| Lidocaine | — | 2.0 | — |

Testing properties of the compositions produced in Examples 1-3 is described below.

Test 1.

The dehydrative activity of the compositions produced in Examples 1-3, was evaluated by dialysis through a semi-permeable polymeric membrane. Sample compositions weighing 0.5 g were put in a chamber, the bottom of which served as semi-permeable membrane, installed in a vessel with 200 ml of distilled water at 37° C. so that the membrane was immersed in water for 2-5 mm. The chamber with the sample and the membrane was weighed before the experiment and then every hour during the day. Dynamics of growth of the mass samples were compared with the highly dispersed silica as shown in FIG. 3.

Figure 3:
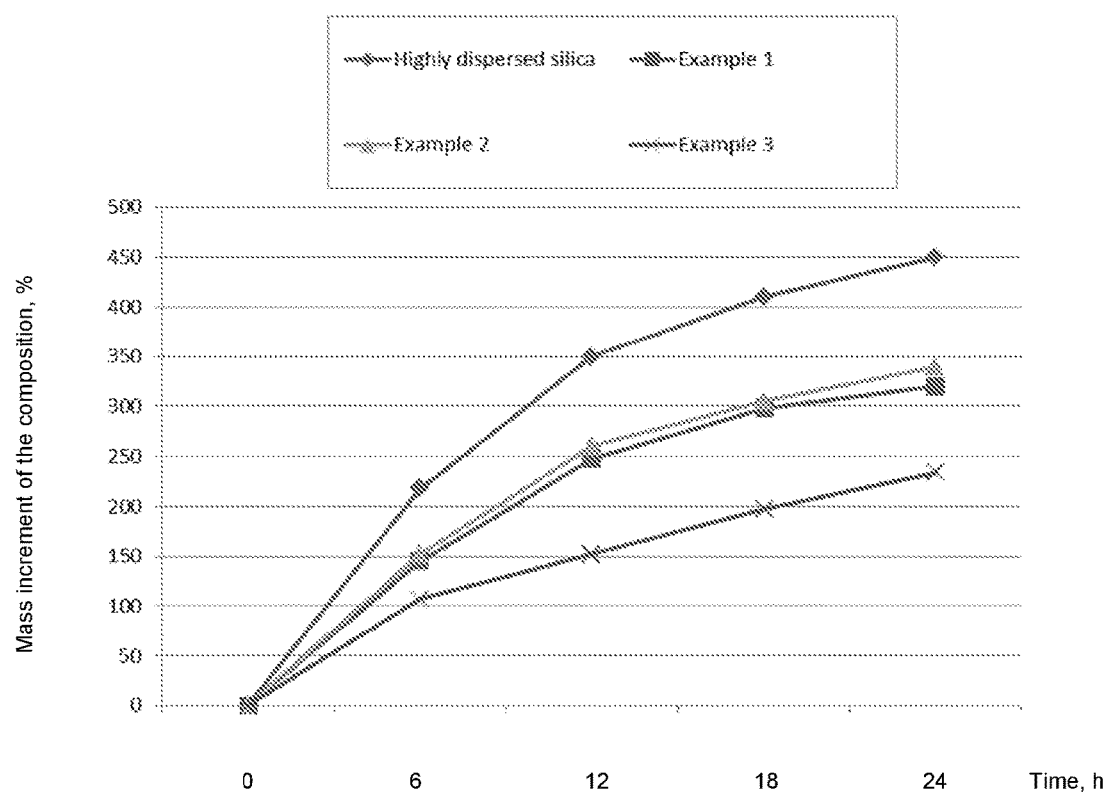
FIG. 3 shows the dehydrative activity of the wound healing compositions of Examples 1 to 3 shown in Table 1 compared to highly dispersed silica alone (in % of mass increment of the composition).

As can be seen in FIG. 3, the dehydrative activity of a composition depends on the content of the hydrophilic highly dispersed silica. Thus, changing the content of a hydrophilic component, the composition can be used in different phases of wound process (more hydrophilic in the first phase, less hydrophilic—in the next phases), thus achieving one of the objectives of the present invention.

Test 2.

To study the protein sorption ability the samples of highly dispersed silica, polymethylsiloxane (pre-lyophilized by adding a few drops of ethanol) and compositions obtained according to Examples 1 to 3 were placed in test-tubes, then 4 ml of 1% solution of gelatin were added to each of the samples and mixtures and moderately stirred during 2 hours, after which the mixtures were centrifuged and the equilibrium concentration of protein in the supernatant was measured by a biuret method. To study the sorption of low molecular weight substances in the test tubes a solution of amino acids (preparation "Aminosteryl") was added instead of gelatin, whose concentration before and after sorption was determined by a photocolorimetric method by reaction with ninhydrin. The sorption capacity was calculated as the difference between the initial and equilibrium concentrations of protein (or amino acids), which can be attributed to 1 g of sorbent. The results are shown in Table 2.

As shown, the protein sorption activity of various compositions was found to gradually increase when the content of highly dispersed silica is raised. Highly dispersed silica on its own has the highest protein sorption activity, while polymethylsiloxane hardly absorbs protein.

Compositions produced by Examples 1 and 2, which have the highest protein sorption and dehydrative ability, should be used for the treatment of purulent wounds with significant exudation, while compositions according to example 3, should be used on wounds with moderate exudation to prevent drying of tissues.

In experiments on the sorption of amino acids the opposite effect was observed: porous hydrophobic polymethylsiloxane reveals highest sorption activity, while highly disperse silica practically does not absorb amino acids. So, the sorption activity of the composition in respect of amino acids decreases with decreasing content of polymethylsiloxane.

Consequently, the ingredients of the composition of the present invention complement each other in their sorption capacity, which allows for more efficient detoxification of wound content.

TABLE 2

The results of the study of sorption properties of different preparations
of the composition (preparations given in Table 1)

| Examined samples | Sorption of gelatin, mg/g | Sorption of amino acids, mg/g |
|---|---|---|
| Highly dispersed silica | 390 | — |
| Preparation for Example 1 | 300 | 6.5 |
| Preparation for Example 2 | 308 | 6.6 |
| Preparation for Example 3 | 120 | 10.2 |
| Polymethylsiloxane | — | 13.5 |

Test 3.

To study the antimicrobial properties of the compositions the agar diffusion test was used ("method of holes"). As a test culture the museum strains of aerobic and anaerobic microorganisms were utilized. Sowing dose in the trials of aerobic microflora was $10^7$ colony forming units (CFU)/ml and in experiments with anaerobes—$10^8$ CFU/ml. Antimicrobial activity was evaluated by the diameter of the zone of stunted growth of colonies on the agar around the hole, which contained the composition. Properties of the composition obtained from Example 1 were tested in comparison with metronidazole, and the composition derived from Example 2 was compared with mupirocin. The results are presented below (Table 3 and 4).

TABLE 3

Antibacterial activity of the composition obtained
in Example 1 against anaerobic microorganisms

| Samples | The diameters of the zones of inhibition, mm (M ± m, n = 3) | | | |
|---|---|---|---|---|
| | *Peptococcus niger* 1 | *Peptostreptococcus anaerobius* 13 | *Prevotella melaninogenica* 97 | *Bacteroides fragilis* ATCC 13/83 |
| Metronidazole | 26.0 ± 0.6 | 26.7 ± 0.6 | 25.7 ± 0.3 | 25.0 ± 0.6 |
| Composition of Example 1 | 28.3 ± 0.3* | 28.0 ± 0.6 | 27.7 ± 0.3* | 27.3 ± 0.3* |

*Reliable difference with respect to rate of metronidazole, $p < 0.05$

As can be seen, the composition obtained in Example 1 is characterized by a rather high activity towards the anaerobic microflora that is not inferior to the initial metronidazole. However, this composition has a medium or insufficient activity against aerobic microorganisms *Staphylococcus aureus* ATCC 25923, *Staphylococcus aureus* ATCC 6538, *Candida albicans* ATCC 885/653, *Echerichia coli* ATCC 225922, *Proteus vulgaris* ATCC 4636, and *Pseudomonas aeruginosa* ATCC 27853/ATCC 9027 (The diameters of the zones of inhibition are less than 15 mm).

For the composition obtained in Example 2, on the contrary, there is a high sensitivity of aerobic microorganisms (Table 4) and a complete lack of sensitivity of anaerobic microorganisms, which naturally characterizes the properties of mupirocin.

TABLE 4

Antibacterial activity of the composition obtained in Example 2 against aerobic microorganisms

| | Minimum inhibitory concentration (MIC) | | | |
|---|---|---|---|---|
| Sample | *Streptococcus pyogenes* 421 | *Staphylococcus aureus* ATCC 25923 | *Proteus vulgaris* X | *Escherichia coli* NTCT 10418 |
| Mupirocin | 0.12 | 0.25 | 64 | 128 |
| Composition of Example 2 | 1 | 4 | 256 | 512 |

Test 4.

Information about interactions between the composition and pathogenic microflora is of special interest. This information is necessary for understanding the healing activity of the composition when applied in the treatment of a purulent necrotic locus.

The interaction of the composition of Example 1 with enteropathogenic *coli bacillus, staphylococcus aureus, proteus vulgaris*, and *pseudomonas aeruginosa* was studied. In this study a 3 ml sample of a one day old culture of microorganisms was taken and the quantities of the composition specified in Table 5 were added, followed by mixing for 2-3 minutes and filtering. Because the sorption of the bacteria by the inventive composition is a rapid effect, the time of mixing shall be not more than 3 minutes in order to limit the antimicrobial effect of the preparation which may otherwise reduce the amount of living bacteria and thereby limit the number of colonies of microorganisms which may grow. The filtrate was seeded quantitatively on the culture media (agar plates) and after 24 hours of incubation at a temperature 37° C., the quantity of grown colonies was calculated which coincided with the quantity of bacteria not adsorbed by the composition.

TABLE 5

Sorption of pathogenic microorganisms in the suspension of the composition made according Example 1.

| Initial suspension of bacteria, CFU*/ml | Concentration of the composition, mg/ml | Quantity of non- adsorbed bacteria, % | | | |
|---|---|---|---|---|---|
| | | E. coli | St. aureus | Pr. vulgaris | Ps. aeruginosa |
| $10^7$ | 5 | 0.92 | 0.81 | 1.04 | 1.32 |
| | 10 | 0.21 | 0.16 | 0.26 | 0.40 |
| | 20 | 0.03 | 0.03 | 0.06 | 0.08 |
| $10^8$ | 5 | 1.38 | 1.02 | 1.18 | 1.42 |
| | 10 | 0.39 | 0.32 | 0.34 | 0.45 |
| | 20 | 0.06 | 0.06 | 0.06 | 0.10 |
| $10^9$ | 5 | 1.84 | 1.36 | 2.30 | 2.60 |
| | 10 | 0.80 | 0.56 | 1.18 | 0.60 |
| | 20 | 0.09 | 0.12 | 0.12 | 0.12 |

*CFU—Colony Forming Units

As a comparative experiment the above experiment was repeated using only the highly dispersed silica (HDS) instead of the composition shown in Table 5. This comparative experiment shows that the highly dispersed silica is the substance which is responsible for the bacteria sorption in composition. The results are shown in Table 5a.

TABLE 5a

Absorption of pathogenic microorganisms in a suspension of highly dispersed silica

| Initial suspension of bacteria, CFU*/ml | Concentration of the HDS, mg/ml | Quantity of non-adsorbed bacteria, % | | | |
|---|---|---|---|---|---|
| | | E. coli | St. aureus | Pr. vulgaris | Ps. aeruginosa |
| $10^7$ | 3.3 | 0.90 | 0.80 | 1.00 | 1.30 |
| | 6.6 | 0.18 | 0.15 | 0.25 | 0.30 |
| | 13.3 | 0.02 | 0.02 | 0.05 | 0.06 |
| $10^8$ | 3.3 | 1.38 | 1.00 | 1.10 | 1.20 |
| | 6.6 | 0.36 | 0.30 | 0.30 | 0.35 |
| | 13.3 | 0.05 | 0.04 | 0.05 | 0.08 |
| $10^9$ | 3.3 | 1.81 | 1.30 | 2.20 | 2.50 |
| | 6.6 | 0.86 | 0.50 | 1.10 | 0.50 |
| | 13.3 | 0.07 | 0.10 | 0.09 | 0.10 |

*CFU—Colony Forming Units

The results of the study displayed in the Tables 5 and 5a show that the composition is able to adsorb almost all microorganisms in the solution when used at a concentration which does not exceed the therapeutic concentration of 40 mg/ml (till $3·10^9$ microbial cells on 1 gram of the composition) regardless of the kind of microorganism. The composition is able to adsorb quickly within a few minutes, not only microorganisms but also products of their metabolism. The composition adsorbs gram-positive cocci and gram-negative bacilli with similar effectivity. The composition does not have a selective absorption effect in respect to different kinds of microorganisms and therefore avoids the risk of selection of certain strains, which could possibly lead to the accumulation of stable strains in the wound.

Thus, the composition without involving its direct antimicrobial effects leads to a significant reduction of pathogenic properties of microorganisms due to its fast and firm sorption which therefore constitutes an important achievement of the present invention regarding the therapeutic action of the composition in the local treatment of purulent wounds.

The invention claimed is:

1. A composition in powder form comprising highly dispersed silica particles, polymethylsiloxane particles, a cationic surfactant and optionally an antimicrobial substance, wherein the following conditions are fulfilled:

a) at least 25% by weight of the cationic surfactant is present in primary polymethylsiloxane particles comprising the cationic surfactant mechanochemically immobilized onto the surface of the primary polymethylsiloxane particles and/or in agglomerates of these primary polymethylsiloxane particles; and optionally b) at least 25% by weight of the antimicrobial substance is present in primary highly dispersed silica particles comprising the antimicrobial substance mechanochemically immobilized onto the surface of a part of the primary highly dispersed silica particles and/or in agglomerates of these primary highly dispersed silica particles.

2. The composition according to claim 1, wherein the composition comprises the highly dispersed silica particles, the polymethylsiloxane particles, the cationic surfactant, and the antimicrobial substance.

3. A composition in powder form obtained by a method comprising the following steps (a) to (c):
(a) providing highly dispersed silica particles, polymethylsiloxane particles, a cationic surfactant and optionally an antimicrobial substance;
(b) carrying out the following step (b1) and optionally (b2):
(b1) forming primary polymethylsiloxane particles carrying the cationic surfactant on the surface of the primary polymethylsiloxane particles and/or agglomerates of the primary polymethylsiloxane particles,
(b2) forming primary highly dispersed silica particles carrying the antimicrobial substance on the surface of the primary highly dispersed silica particles and/or agglomerates of the primary highly dispersed silica particles using a minor part of the highly dispersed silica particles; and
(c) mixing a major part of the highly dispersed silica particles with the products obtained in step (b), wherein the formation of the primary particles in steps (b1) and optionally (b2) is achieved by milling the respective components.

4. The composition according to claim 3, wherein the major part of the highly dispersed silica particles employed in step (c) represents 70 to 95 wt. % of the total weight of the highly dispersed silica comprised in the composition and, when step (b2) is carried out, the remaining highly dispersed silica particles form the minor part of the highly dispersed silica particles employed in step (b2).

5. The composition according to claim 1, wherein the composition comprises
21.0 to 75.0 wt. % of the highly dispersed silica,
16.0 to 70.0 wt. % of the polymethylsiloxane, and
at least one of a cationic surfactant in an amount of 0.2 to 4.0 wt. %, and an antimicrobial substance in an amount of 0.5 to 10 wt. %,
based on the total weight of the composition.

6. The composition according to claim 1, wherein the composition further comprises at least one of the following agents:
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

7. The composition according to claim 3, wherein in step (b2) the primary particles of the highly dispersed silica carry the antimicrobial substance and at least one further substance selected from the group consisting of compounds having tissue growth activity, lidocaine, and phenothiazine derivatives on their surface.

8. The composition according to claim 3, wherein in step (c) the major part of the highly dispersed silica is mixed with the products obtained from step (b) and at least one component selected from zinc oxide, and proteolytic enzymes.

9. The composition according to claim 3, wherein
in step (b2) the antimicrobial substance and at least one further substance selected from the group consisting of compounds having tissue growth activity, lidocaine, and phenothiazine derivatives are mechanochemically immobilized onto the highly dispersed silica particles.

10. The composition according to claim 1, wherein the sum of the highly dispersed silica and the polymethylsiloxane represents 65 to 97 wt of the total weight of the composition.

11. A pharmaceutical preparation which is or comprises the composition of claim 1.

12. A medical article selected from the group consisting of a dressing, packets, or capsules, comprising the pharmaceutical preparation according to claim 11.

13. A method for the treatment of purulent wounds and necrotic wounds in a subject, the method comprising applying the composition according to claim 1 to the subject.

14. A method for the treatment of at least one condition in a subject, wherein the condition is selected from the group consisting of infected burn surfaces, putrid necrotizing phlegmons and noma in the maxillofacial region, wounds during a larynx or laryngopharynx resection after a cancer surgery, inflammatory diseases of the throat, mouth cavity and/or teeth, pharyngitis, tonsillitis, gingivitis and stomatitis, periodontitis, dental application and ultraphoresis, diseases of the rectum, the large intestine and organs of abdominal cavity, peritonitis, intra-abdominal and pancreatogenic abscesses, complications after pancreatonecrosis, extraperitoneal phlegmons, inflammatory diseases of the uterus and uterine adnexa, urinary bladder, pleura, bones, and other visceral organs, osteomyelitis, urethritis caused by gonococci, trichomonases and other infections, diseases in the front part of the eyes, a fistular in traumatic surgery, food intoxication, acute intestinal obstruction and intoxications by a virus, wounds and impetiginous diseases of the skin, acne, folliculitis and sycosis in the face and/or diseases provoked by irrational application of cosmetics, hemorrhoids, proctitis, anorectal abscesses, anal fissures, wounds after gynecological surgeries, non-specific trichomonal and fungal colpitis, vaginitis, vulvitis, metritis, parametritis, salpingitis, infectious diarrhea, infections caused by *staphylococcus aureus*, methicillin-resistant *staphylococcus aureus* (MRSA), multi-resistant gram-negative bacteria, enterobacteriaceae, and non-fermenting bacteria, the method comprising applying the composition according to claim 1 to the subject.

15. The method according to claim 3, wherein the milling is carried out using a ball mill or a vibrational mill.

16. The method according to claim 15, wherein the milling in step (b1) is carried out using a ball mill comprising a drum, wherein the time of milling is 30 to 60 minutes, and the speed of rotation of the drum in 0.5 to 2 revolutions per second (rev/sec).

17. The method according to claim 15, wherein the milling in step (b1) is carried out using a ball mill comprising a drum, wherein the time of milling is 30 to 60 minutes, and the speed of rotation of the drum in 0.5 to 2 revolutions per second (rev/sec).

* * * * *